United States Patent
Trauner et al.

(10) Patent No.: US 11,666,447 B1
(45) Date of Patent: *Jun. 6, 2023

(54) BONE IMPLANT AUGMENT AND OFFSET DEVICE

(71) Applicant: Taq Ortho, LLC, San Francisco, CA (US)

(72) Inventors: Kenneth B. Trauner, San Francisco, CA (US); Bradford J Coale, Chester, NJ (US)

(73) Assignee: Taq Ortho, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/878,544

(22) Filed: Aug. 1, 2022

Related U.S. Application Data

(63) Continuation-in-part of application No. 17/069,678, filed on Oct. 13, 2020, which is a continuation-in-part
(Continued)

(51) Int. Cl.
*A61F 2/36* (2006.01)
*A61F 2/46* (2006.01)

(52) U.S. Cl.
CPC .............. *A61F 2/36* (2013.01); *A61F 2/3676* (2013.01); *A61F 2002/4631* (2013.01)

(58) Field of Classification Search
CPC ... A61F 2/36; A61F 2/3676; A61F 2002/4631
See application file for complete search history.

(56) References Cited

U.S. PATENT DOCUMENTS 5,026,373 A * 6/1991 Ray ..................... A61B 17/1637
606/279
5,652,056 A * 7/1997 Pepin .................... A61L 27/425
423/311
(Continued)

FOREIGN PATENT DOCUMENTS

EP 2522299 A1 * 11/2012 ............. A61C 8/005

OTHER PUBLICATIONS

"Notification of Transmittal of the International Search Report and the Written Opinion of the International Searching Authority, or the Declaration"; International Application No. PCT/US22/40466, International Application Filing Date: Aug. 16, 2022, Applicant: Trauner, Kenneth B.
(Continued)

*Primary Examiner* — Keri J Nelson
*Assistant Examiner* — Melissa A Hoban
(74) *Attorney, Agent, or Firm* — Staniford Tomita LLP

(57) ABSTRACT

A bone insert includes a cap having a convex top surface made from a plurality of cap micro struts, an elongated stem made from a plurality of stem micro struts, and a barrier between the cap and the stem. The stem of the bone insert is inserted into a hole formed in a host bone until the barrier is pressed against the exposed bone. The bone implant can be placed against a small focus contact point on the cap. Liquid cement can be injected into a large center hole in the cap and the cement can flow through the fenestrations between all of the cap micro struts as well as the space between the bone implant and the bone. The cement can cure to create a high strength structure that provides a strong bond between the bone implant and the host bone.

20 Claims, 16 Drawing Sheets

Related U.S. Application Data of application No. 15/582,380, filed on Apr. 28, 2017, now Pat. No. 10,799,369, which is a continuation-in-part of application No. 15/059,511, filed on Mar. 3, 2016, now abandoned.

(60) Provisional application No. 63/239,742, filed on Sep. 1, 2021, provisional application No. 62/237,018, filed on Oct. 5, 2015, provisional application No. 62/133,072, filed on Mar. 13, 2015, provisional application No. 62/328,799, filed on Apr. 28, 2016, provisional application No. 62/128,732, filed on Mar. 5, 2015.

(56) References Cited

U.S. PATENT DOCUMENTS

| | | | | |
|---|---|---|---|---|
| 5,702,487 | A | 12/1997 | Averill et al. | |
| 5,709,683 | A * | 1/1998 | Bagby | A61F 2/44 623/17.11 |
| 6,149,651 | A * | 11/2000 | Drewry | A61F 2/446 606/247 |
| 6,193,755 | B1 * | 2/2001 | Metz-Stavenhagen | A61F 2/4611 623/17.11 |
| 7,666,230 | B2 * | 2/2010 | Orban | A61F 2/30756 623/23.75 |
| 8,163,032 | B2 * | 4/2012 | Evans | A61L 31/042 623/23.61 |
| 8,292,968 | B2 * | 10/2012 | Truncale | A61L 27/48 623/23.51 |
| 8,480,757 | B2 * | 7/2013 | Gage | A61L 27/3641 623/23.55 |
| 8,906,110 | B2 * | 12/2014 | Semler | A61L 27/3608 623/23.72 |
| 8,968,404 | B2 * | 3/2015 | Dee | A61F 2/389 606/86 R |
| 9,327,056 | B2 * | 5/2016 | Bandyopadhyay | B33Y 70/10 |
| 10,610,364 | B2 * | 4/2020 | Dee | A61F 2/38 |
| 11,298,235 | B2 * | 4/2022 | Dee | A61F 2/389 |
| 11,458,228 | B2 * | 10/2022 | Piecuch | A61L 27/047 |
| 2002/0010511 | A1 * | 1/2002 | Michelson | A61F 2/446 623/17.15 |
| 2002/0183858 | A1 * | 12/2002 | Contiliano | A61L 27/58 623/23.76 |
| 2003/0004578 | A1 * | 1/2003 | Brown | A61L 27/425 623/23.72 |
| 2003/0055316 | A1 * | 3/2003 | Brannon | A61B 1/313 600/114 |
| 2003/0236573 | A1 * | 12/2003 | Evans | A61F 2/4601 623/23.63 |
| 2005/0004572 | A1 * | 1/2005 | Biedermann | A61F 2/44 606/247 |
| 2005/0060037 | A1 * | 3/2005 | Michelson | A61F 2/4455 623/17.15 |
| 2005/0064042 | A1 * | 3/2005 | Vunjak-Novakovic | A61P 19/00 424/549 |
| 2005/0112397 | A1 * | 5/2005 | Rolfe | A61F 2/4455 606/76 |
| 2005/0125073 | A1 * | 6/2005 | Orban | A61F 2/30756 623/23.58 |
| 2005/0267591 | A1 * | 12/2005 | Ricci | A61M 39/0247 623/23.44 |
| 2006/0093646 | A1 * | 5/2006 | Cima | A61L 27/54 606/76 |
| 2006/0216323 | A1 * | 9/2006 | Knaack | C08G 18/6484 525/54.1 |
| 2006/0241776 | A1 * | 10/2006 | Brown | A61B 17/7225 623/22.32 |
| 2007/0162027 | A1 * | 7/2007 | Chappuis | A61B 17/70 606/86 A |
| 2007/0203584 | A1 * | 8/2007 | Bandyopadhyay | B22F 3/105 623/901 |
| 2008/0051796 | A1 * | 2/2008 | Nycz | A61L 31/148 606/86 R |
| 2008/0077248 | A1 * | 3/2008 | Murillo | A61F 2/44 623/17.16 |
| 2008/0077251 | A1 * | 3/2008 | Chen | A61F 2/4644 623/23.72 |
| 2009/0024229 | A1 * | 1/2009 | Chen | A61F 2/28 623/23.72 |
| 2009/0319045 | A1 * | 12/2009 | Truncale | A61L 27/48 623/23.73 |
| 2010/0191340 | A1 * | 7/2010 | Dreyfuss | A61F 2/4612 606/86 R |
| 2012/0172880 | A1 * | 7/2012 | Dee | A61B 17/562 606/87 |
| 2014/0277544 | A1 * | 9/2014 | Viscogliosi | A61F 2/389 606/86 R |
| 2014/0288650 | A1 * | 9/2014 | Hunt | A61F 2/447 623/16.11 |
| 2016/0256280 | A1 * | 9/2016 | Trauner | A61F 2/4601 |
| 2017/0296358 | A1 * | 10/2017 | Trauner | A61F 2/38 |
| 2018/0092677 | A1 | 4/2018 | Peterson et al. | |
| 2018/0214192 | A1 | 8/2018 | Roby et al. | |
| 2019/0076257 | A1 * | 3/2019 | Dee | A61F 2/4618 |
| 2019/0099515 | A1 * | 4/2019 | Bagga | A61L 27/56 |
| 2020/0315662 | A1 | 10/2020 | Adam et al. | |
| 2020/0330234 | A1 * | 10/2020 | Dee | A61F 2/30756 |
| 2021/0000602 | A1 * | 1/2021 | Kumta | A61F 2/3094 |
| 2021/0153911 | A1 | 5/2021 | Stuart et al. | |
| 2021/0378834 | A1 * | 12/2021 | Kleiner | A61F 2/30771 |
| 2022/0296376 | A1 * | 9/2022 | Dee | A61F 2/40 |

OTHER PUBLICATIONS

Milligan et al. "The effects of age and gender on the diameter of the femoral canal in patients who undergo total hip replacement". Bone Joint J. Mar. 2013;95-B(3):339-42. doi: 10.1302/0301-620X.95B3. 30882. Retrieved Oct. 31, 2022.

* cited by examiner

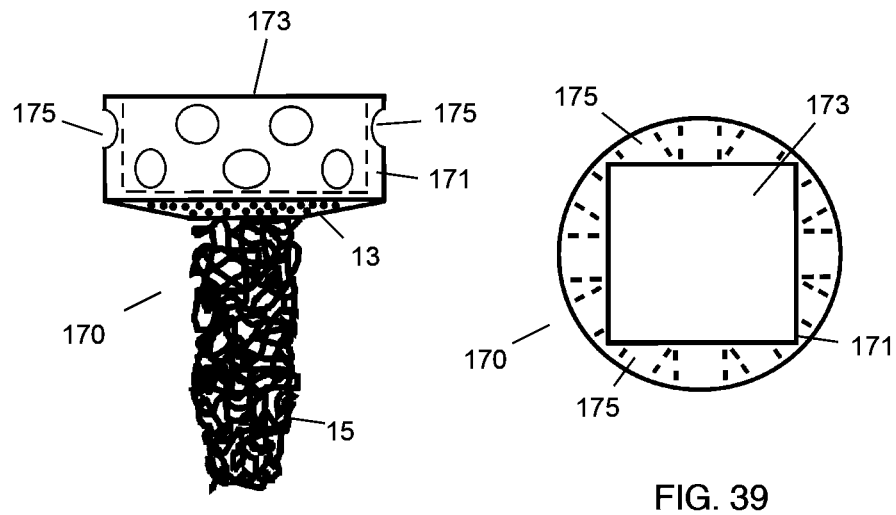
FIG. 38
FIG. 39
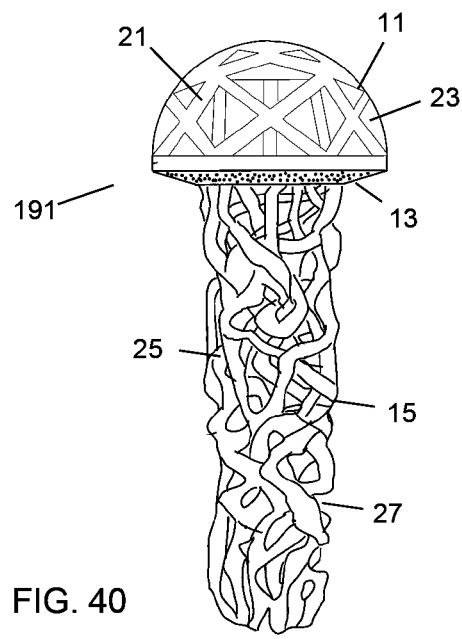
FIG. 40

BONE IMPLANT AUGMENT AND OFFSET DEVICE

CROSS REFERENCE TO RELATED APPLICATIONS

This patent application is a continuation-in-part of U.S. patent application Ser. No. 17/069,678, "Bone Implant Augment Method And Apparatus" filed Oct. 13, 2020, which is a continuation-in-part of U.S. patent application Ser. No. 15/582,380, "Bone Implant Augment Method And Apparatus" filed Apr. 28, 2017 which is now U.S. Pat. No. 10,799,369 which claims priority to Application No. 62/328,799, "Bone Implant Augment Method And Apparatus" filed Apr. 28, 2016. This application is also a continuation in part of U.S. patent application Ser. No. 15/059,511, "Bone Implant Augment Method And Apparatus" filed Mar. 3, 2016, which claims priority to U.S. Provisional Patent Application No. 62/128,732, "PMMA Shims For Total Knee Arthroplasty" filed Mar. 5, 2015, U.S. Provisional Patent Application No. 62/133,072, "PMMA Shims For Total Knee Arthroplasty" filed Mar. 13, 2015, and U.S. Provisional Patent Application No. 62/237,018, "Shims Augment System" filed Oct. 5, 2015. This application claims priority to U.S. Provisional Patent Application No. 63/239,742, "Cement Fixation Augment And Or Offset Device" filed Sep. 1, 2021 which is hereby incorporated by reference in its entirety. U.S. patent application Ser. Nos. 17/069,678, 15/582,380, 15/059,511, 62/328,799, 62/237,018, 63/239,742, 62/133,072, and 62/128,732 are hereby incorporated by reference in their entireties.

BACKGROUND

The proper functioning of a joint, such as the knee, hip, shoulder, ankle or elbow can be impeded by a variety of factors, including, disease, such as osteoarthritis, mechanical injury, bone deformation and a variety of other factors. Arthroplasty, or the surgical restoration of a joint, is a known procedure that is often used to relieve pain and improve joint function by replacing the diseased or damaged articulating surfaces of a joint with prosthetic components. Achieving stable joint balance is a primary goal for arthroplasty surgeons. A balanced joint is a joint that has the proper articulation and ligamentous balance in all orientations of the joint. The patient may be most comfortable when the artificial joint replicates the kinematics of the original, natural joint.

Various bone implant devices have been developed for orthopedic surgery. For example, a surgical implant can include an augment for the fixation of cemented total joint replacements. poly(methyl methacrylate) (PMMA) is used as the standard for cementing total joint implants to the bone of patients. More specifically, a solid metal bone augment spacer device for adjusting the position can be screwed to a bone implant. Liquid PMMA can be applied to the contact areas of the bone, bone implant, and solid metal screw device. The PMMA can then cure to secure bone implant device to the bone. The bone implant and solid metal screw spacer do not have bone ingrowth surfaces and do not stabilize the cement mantle.

However, PMMA cementing and bone implant failures can occur when the implanted bone is less porous, when the bone is hard or more sclerotic. In sclerotic bone the cement does not interdigitate or penetrate the bone in a manner in which the implant fixation is securely attached to the bone with enough strength to resist the high repetitive forces between the bone and cement mantle. What is needed are bone inserts that can be inserted into the bone and used to improve the bonding of the bone implant to the bone and method for attaching the bone insert and bone implant to the bone of the patient that addresses the defects with the prior art, produces offsets at virtually any location of the bone, improves the stability of the cement and is less prone to failure. Specifically, the bone insert also interdigitates with the cement in securing the bone insert to the cement, while the interdigitation with the cement produces a composite construct the resists breakdown at the cement insert interface with cyclic loading and resists pullout of the insert from the cement.

SUMMARY OF THE INVENTION

The present invention is directed towards an improved bone insert and an installation technique for improving the cement fixation of the bone implant to the bone insert to host bone. A bone implant can be a medical device that is permanently attached to the bone of a patient. The bone implant can be a replacement joint such as an artificial knee which can be made of multiple metal components. A bone insert can be a structure that is placed into a hole formed in a bone of the patient that provides structural support and improved bonding strength between the bone implant and the bone of the patient when used with liquid cement such as PMMA. The inventive bone insert can include a cap and an elongated stem that are highly porous structures that are coupled to each other and separated by a barrier structure. A hole can be formed in the host bone and the stem portion of the bone insert can be inserted into the hole of the host bone of the patient. The barrier structure of the bone insert can be placed against the surfaces of the host bone surrounding the hole and can prevent liquids from flowing into the hole. The cap of the bone insert can be a curved convex surface. For example, in some embodiments, the convex surface can be a convex spherical or aspherical surface that provides a small exposed focal point or focal spot offset contact surface area upon which the implant structure can be placed on. The small focal point contact surface area between the bone insert and the bone implant is important because it minimizes the contact area between these metal components. Movement between the bone insert and the bone implant results in friction and wear of these components at the contact areas. By minimizing the contact area, the friction and wear of these components is also reduced and minimized.

It can be important to have a convex top surface on a bone insert having a cap diameter that is greater than 6 mm in order to have a small focal point of contact. However, the convex surface of the top surface of the cap can be less important when the diameter of the cap is equal to or less than 6 mm. More specifically, a cap having a diameter less than 6 mm can provide a small focal point of contact even if the upper surface is flat rather than convex. In other embodiments, the cap can have a diameter of between 5 mm and 60 mm or greater.

Liquid cement such as PMMA can be placed on the cap, the bonding surface(s) of the bone implant and the resection surfaces of the host bone. The barrier of the bone insert can prevent the liquid cement from flowing into the elongated stem portion of the bone insert and the hole of the host bone. The liquid cement can then be cured to bond and secure the bone implant structure to the cap of the bone insert and to the host bone. The lower surface of the barrier can have a bone ingrowth surface and the host bone can grow into these bone ingrowth features at the contact areas with the barrier structure. Similarly, the stem can also have bone ingrowth features and the host bone can grow into these features at the inner surfaces of the hole formed in the bone.

The cap can be made of a plurality of cap micro struts that form a three dimensional lattice structure can include straight or curved struts that can be uniform in cross section such as a circular cross section. The plurality of cap micro struts can be coupled to each other. The cap micro struts can form a plurality of tetrahedrons, three dimensional polygons, and convex polytopes that are joined to form the cap structure. The cap micro struts three dimensional structures that are used to create the cap can be symmetric. In some embodiments, the cap can have a hemispherical shape. The sides of the cap can have roughly a cylindrical shape formed from the outer facing surfaces of the cap micro struts. The cap micro struts can be between 50-500 microns in diameter. The cap can be formed by the cap micro struts and the volume of empty space between the cap micro struts is greater than half the volume of the cap micro struts. Thus, the cap micro struts can have less than 33% of the total cap volume and the open space between the cap micro struts is greater 66% of the total cap volume. The cap micro struts can also be textured to enhance the bonding to cements such as PMMA.

In other embodiments, the cap can be made from other non-strut structures such as a textured hollow hemispherical shell or a solid cap structure. The hollow or solid cap can have a center liquid cement inlet hole and other fenestrations in the hemispherical shell for allowing the liquid cement to flow out of the cap volume. The center hole can also match the size and cross section shape of an insert tool. The texturing of the hemispherical shell can enhance the bonding of the cap to the cured cement.

The elongated stem can be made of many stem micro struts with ingrowth fenestrations stem micro struts and surface texture features on outer surfaces of the stem micro struts. The textured surfaces of the stem can provide help to secure the bone insert to the bone. In some embodiments, the stem can have a tapered stem that can be press fit into the bone so that the outer surface of the stem creates bone ingrowth surfaces. The bone material on the inner diameter of the hole formed in the host bone can also grow into the ingrowth fenestrations in the stem between the spaces between the adjacent stem micro struts to permanently bond the bone insert into the bone of the patient. The inventive bone inserts can provide increased pullout strength (resistance to pullout) of the implant from cement with a composite multiplanar beam structure. In different embodiments, the stem can have a diameter between 2 mm and 30 mm or more.

The stem micro struts are coupled to each other to form a structure that can have a modulus of elasticity that matches or is similar to the modulus of elasticity of the host bone. The elongated stem can have an elongated cylindrical shape formed from the outer facing surfaces of the stem micro struts. The stem micro struts can be non-linear and bent and/or curved. The stem micro struts can also be non-uniform in cross section. The elongated stem can be a straight cylinder or a tapered cylinder that can fit into a hole drilled into a bone. The stem micro struts can form a bone implant structure that is designed to match specific mechanical properties of a bone that the implant is inserted into. When a force is applied to the bone insert, the strain of the bone insert can match the strain on the bone to minimize movement between the bone and the bone insert. The surfaces of the stem micro struts can have a textured surface or a surface roughness that can promote friction bonding of the elongated stem to the bone and ingrowth of bone material into the elongated stem.

In some embodiments, the elongated stem can have a helical threaded surface that can be rotated to screw the elongates stem to drive the elongated stem into the bone. In some embodiments, the helical thread can be machined into the stem portion of the bone insert. Alternatively, the helical thread can be formed in the outer facing surfaces of the stem through the bone insert manufacturing method. For example, in some embodiments the bone inserts are designed with the assistance of computer algorithms that provide the stem micro struts that have helical threads on the outer facing surfaces.

In other embodiments, the elongated stem can be made from other non-strut structures. For example, the elongated stem can be a textured porous hollow or solid structure. The hollow or solid elongated stem can have fenestrations to allow bone ingrowth. The texturing of the hemispherical shell can enhance the physical coupling to the bone when the insert is initially inserted into the bone and provide bone ingrowth surfaces to further improve bonding when the bone grows into the textured surfaces. The fenestrations in the elongated stem can enhance the bonding as the bone grows into the fenestrations.

The bone inserts can be fabricated with 3D printing machines such as: direct metal laser sintering (DMLS), selective laser melting (SLM), electron beam melting (EBM), laser metal deposition (LMD), selective laser sintering (SLS), binder jetting, metal injection molding, and any other known 3D metal fabrication processing machines using either direct or indirect manufacturing techniques. The inserts can also be made using other methods for creation of porous metal structures. The bone inserts can be made of surgical grade metal materials such as titanium, tantalum, or any other suitable metal material. The inserts may also be made of polymer materials that are known to ingrow with bone such as polyetheretherketone (PEEK) and polyetherketoneketone (PEKK). In some embodiments, the PEEK or PEKK can be provided as a homogeneous filament material which can be 3D printed with a plastic compatible 3D printing machine such as a Fused filament fabrication (FFF), fused deposition modeling (FDM), other suitable 3D printer machines. Alternatively, the PEEK or PEKK can be provided as a homogeneous powder that can be fabricated into the described bone inserts using an SLS machine or other suitable 3D printer machines.

In some embodiments, the barrier can be a circular structure between the cap and the elongated stem. The barrier can be a solid structure that can prevent the liquid cement from flowing from the cap to the elongated stem. The barrier can also provide an impact surface structure that can allow a tool to press the elongated stem of the bone insert into a bone of a patient. The bottom surface of the barrier that is placed against the host bone can have a textured surface that can allow bone ingrowth. In some embodiments, the barrier can have a locking mechanism that can be secured to the end of the insertion tool. The locking mechanism can be coupled to the insertion tool to pull and extract the bone insert from the bone.

For joint replacement surgeries such as total knee replacements, there are three Morgan Jones zones of fixation. Zone 1 is the epiphysis or joint surface, zone 2 is the metaphysis, and zone 3 is the diaphysis. In a zone 1 region of total joint arthroplasty. The inventive bone insert devices can not only be used to improve fixation but can also produce offsets from bone surfaces. The inventive bone inserts can provide improved strength characteristics for the cement interface between the implant and the bone.

Wolff's law states that a bone in a healthy animal will adapt to the loads under which it is placed. Thus, a bone placed under high loads will become stronger than a bone that is not exposed to high loads. Current bone implants are designed or resist fatigue and as such the bone implants can have much higher modulus of elasticity and stiffness than the surrounding bone. These differences in the modulus of elasticity and stiffness can lead to stress shielding and future bone loss. Furthermore, a mismatch in modulus between the cement and the stiffer bone implant such as the screw or rigid cage leads to increased stresses in the cement and a breakdown of the cement over time. The inventive bone inserts can have stems that formed from a plurality of stem micro struts that are designed to have a modulus of elasticity that matches the modulus of elasticity of the host bone. By matching the modulus of elasticity, the movement and forces between the bone inserts and the host bone are minimized which can extend the life of the bone implant.

There are various other benefits to the inventive bone inserts. The bone insert both secures the cement mantle to the host bone and creates resistance to breakdown of the cement at a specific location. The thin cap micro struts can maximize the surface area interdigitation of the metal with the PMMA cement to create a mechanical interlock. The thin cap micro struts can also have mechanical properties more closely matching that of PMMA than a more solid cap construct. When the PMMA cement cures, a solid composite cap structure is created that is much more resistant to surface crack propagation than a pure cured PMMA cement structure. Cracks are a common mechanism of failure of PMMA in total joint patients as a result of prolonged cyclic loads applied to a brittle cement material. The cracks result in loosening of the bone implant at the bone cement interface. The inventive bone insert prevents the cracks from propagating through the cement at the composite cap of the bone insert which greatly improves the integrity of the bone implant.

BRIEF DESCRIPTION OF THE DRAWINGS

FIG. 38 illustrates a side view of an embodiment of a bone insert.

FIG. 39 illustrates a top view of an embodiment of a bone insert.

FIG. 40 illustrates a side view of an embodiment of a bone insert having a hemispherical cap.

DETAILED DESCRIPTION

This invention describes a novel bone insert for ingrowth into host bone that bridges the gap with the cement mantle connecting to the orthopedic joint implant. The properties of the insert provide stem portions of the bone inserts with improved modulus of elasticity matching with the host bone and modulus of elasticity matching with the cement mantle to improve ingrowth and reduce cement breakdown. The porosity of the inventive bone insert device allows for diffuse interdigitation of the cement with the device and porosity of the bone facing surfaces of the stem promotes bone ingrowth.

Figure 1:
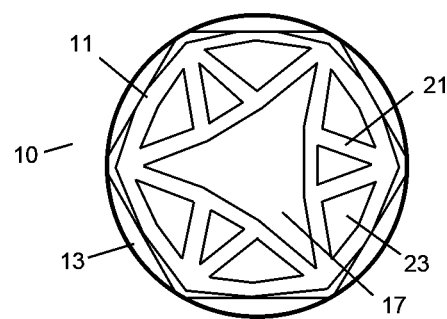
FIG. 1 illustrates a top view of an embodiment of a bone insert.
Figure 2:
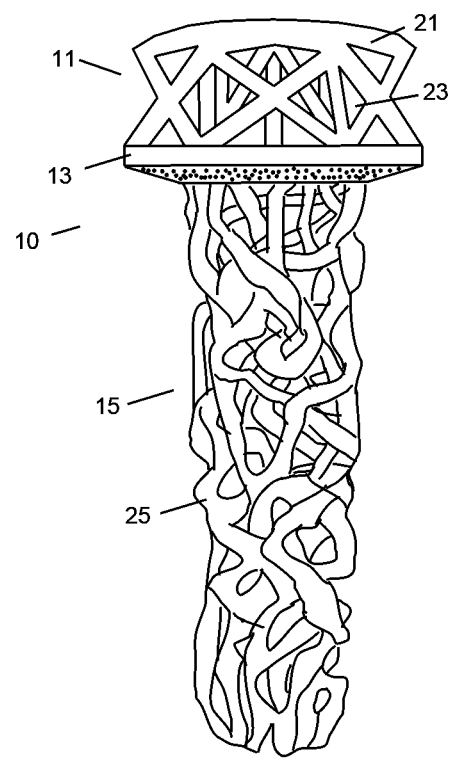
FIG. 2 illustrates a side view of an embodiment of a bone insert.

FIG. 1 illustrates a top view and FIG. 2 illustrates a side view of an embodiment of a bone insert 10 having a cap 11, a stem 15, and a barrier structure 13 between the cap 11 and the stem 15. In the illustrated example, the cap 11 is formed from a plurality cap micro struts 21 that are coupled to each other to form a lattice structure having a plurality of cap fenestrations 23 between the cap micro struts 21. The cap fenestrations 23 can be sized to allow liquid cement such as PMMA to easily flow through the entire lattice of cap micro struts 21 and fill all of the cap fenestrations 23.

In the illustrated embodiment, the cap 11 can have a symmetric geometric shape formed from the cap micro struts 21 on the outer surfaces of the cap 11. The outward surfaces of the outer cap micro struts can form a cylindrical or hexagonal cross section and a convex upper surface. The cap micro struts 21 can be rigidly attached to each other and the barrier 13 at their ends and middle portions to form a high strength array. The cap micro struts 21 can be straight elongated structures that have uniform cross sections. In the illustrated embodiment, the cross sections of the cap micro struts 21 are circular. However, in other embodiments, the cap can be any other shape and the micro struts can have any cross section shape. The volume of the cap 11 can be defined by the outward facing surfaces of the cap micro struts 21. The cap can be formed by the cap micro struts and the volume of empty space between the cap micro struts is greater than half the volume of the cap micro struts. The volume of the cap micro struts 21 can be 33 percent or less of the total volume of the cap 11 with the remaining 66 percent or more of the total volume being open cap fenestration 23 space. A higher percentage of open cap fenestration 23 space is better for protection purposes. The outer surfaces of the cap micro struts 21 can have a texture or a coating that can promote adhesion to cements such as PMMA.

With reference to FIG. 1, the cap micro struts 21 can form a center insertion tool recess 17 in the upper surface of the cap 11. The cap micro struts 21 may have straight and/or curved shapes. The upper surface of the cap 11 can be comprised of curved cap micro struts 21 that can form a convex hemispherical or hemi-aspherical curved upper surface. The contact surface area is minimized to a small focal location point of contact area where the upper surface of the cap 11 contacts a flat undersurface of the bone implant. While the caps 11 are illustrated as having a convex top surface in order to have a small focal point of contact. In other embodiments, the top surface of the cap 11 can be flat or planar when the diameter of the cap 11 is less than or equal to 6 mm. The convex surface of the top surface can be less important when the diameter of the cap 11 is smaller than 6 mm because these smaller diameter caps 11 can provide a small focal point of contact with the bone implant regardless of the cap 11 shape.

In the illustrated embodiment, the center insertion tool recess 17 can be triangular in shape. The center insertion tool recess 17 can be free of all cap micro struts so that the distal tip of the insert tool can be placed between the cap micro struts 21 and pressed against the upper center portion of the barrier structure 13. In the illustrated embodiments, the center axis of the cap 11, barrier 13, and stem 15 of the bone insert 10 can all be aligned about a common center axis.

The lower ends of the cap micro struts 21 can be rigidly attached to an upper surface of the barrier structure 13 and the stem micro struts 21 at the upper end of the elongated stem 15 are coupled to the bottom surface of the barrier structure 13. The barrier structure 13 can have a thin disc circular shape that can be planar, concave, or convex in shape. The barrier structure 13 can be solid or porous to gases. However, in a preferred embodiment, the barrier structure 13 should prevent liquids such as PMMA from flowing through the barrier structure 13. The cap micro struts 21 can be radially symmetric about the center axis of the bone insert. Similarly, the cap fenestrations 23 between the cap micro struts 21 can be arranged symmetrically about the center axis of the bone insert 11. The cap 11 can also have cap micro struts that are oblique supporting struts. The cap fenestrations can create surrounding apertures of the cap 11.

The elongated stem 15 can be a cylindrical structure coupled to an opposite side of the barrier structure 13 from the cap 11. The elongated stem 15 can be created from a plurality of stem micro struts 25 with the exterior surfaces of the stem micro struts 25 that face outward defining a roughly cylindrical or slightly tapered stem volume. In some embodiments, a helical thread can be formed on the outward facing stem micro struts 25 so that the bone insert 10 can be screwed into a hole formed in a bone of a patient. The stem of the bone inserts can be made of a metal material that has surface features that promotes bone ingrowth and/or ongrowth. The stem can be made of titanium or tantalum and the surface features of the stem can include 40-800 micron depth: recesses, grooves, or other surface features such as diameter, width and/or depth.

The volume of the elongated stem 15 can be defined by the outward facing surfaces of the stem micro struts 25. The volume of the stem micro struts 25 can be 40 percent or less of the total volume of the elongated stem 15 with the remaining 60 percent or more of the total volume being open stem fenestration 27 space. The outer surfaces of the cap micro struts 21 can have a texture or a coating that can promote adhesion to cements such as PMMA.

In contrast to the cap micro struts 21, the stem micro struts 25 can be bent and non-linear. The stem micro struts 25 can have specific designs and shapes that form a structure that can be similar or match the physical characteristics of the bone. For example, the stem micro struts 25 of the elongated stem 15 can have a modulus of elasticity that matches the modulus of elasticity of the bone that the bone insert 10 is inserted into. This physical characteristic matching can improve the performance and life of the bone insert 10. When the bone insert is stressed, the bone and a bone insert 10 will deflect in strain. If there is a mismatch between the strain of the bone and the strain of the bone insert 10, there will be some relative stress and/or movement between the bone and the bone insert 10. This stress or movement can result in weakening of the bond between the bone and the bone insert 10. However, if the modulus of elasticity of the bone insert 10 matches the modulus of elasticity of the bone the relative stress and movement is minimized and there is much less weakening of the bond between the bone and the bone insert 10.

The mechanical properties of a typical human femoral cortical bone in a longitudinal and a transverse direction are listed below in Table 1. The data for the elastic modulus was obtained from the National Library of Medicine, National Center for Biotechology Information https://www.ncbi.nlm-.nih.gov/pmc/articles/PMC6053074/

TABLE 1

| | | |
|---|---|---|
| Longitudinal Direction | Elastic Modulus | 10,000-23,00 MPa |
| Transverse Direction | Elastic Modulus | 3,270-12,500 MPa |

Because elastic modulus of the bone can have a wide range of values, the bone inserts 10 can be fabricated with various different predetermined or custom fabricated elastic modulus values. In some embodiments, the surgeon can measure or estimate the modulus of elasticity of the bone prior to selecting the bone insert 10. A surgeon can then select a bone insert 10 for the patient that can most closely match the modulus of elasticity of the bone that the bone insert 10 is inserted into. Alternatively, a custom bone insert 10 can be fabricated for the patient that can match the modulus of elasticity of the bone that the bone insert 10 is inserted into.

As illustrated in Table 1, the longitudinal and transverse elastic modulus values of a human bone can be asymmetric with different with the longitudinal elastic modulus having a higher value than the transverse elastic modulus. This is substantially different than bone insert stems that have uniform and/or homogeneous solid structures. In some embodiments, the elongated stems 15 of the bone inserts 10 can be designed using a computer aided design (CAD) software and the assembly of strut micro struts 25 forming the stem of the bone insert 10 can be analyzed using finite element modeling to determine the longitudinal and transverse elastic modulus values for the elongated stems 15. The designs of the strut micro struts 25 can be adjusted in the CAD system to create longitudinal and transverse elastic modulus values that match the desired values that can match the measured longitudinal and transverse elastic modulus values of the patient's bone.

It is also possible to design and fabricate bone inserts 10 having different elongated stem 15 designs. These different bone inserts 10 can be fabricated by 3D printing and then the elongated stems 15 can be empirically measured to determine the longitudinal and transverse elastic modulus values with mechanical test equipment. The designs of the elongated stems 15 can then be adjusted and fabricated in iterative processes until the desired longitudinal and transverse elastic modulus values are obtained.

The In contrast to the described asymmetric elastic characteristics, an elongated stem having a uniform construction can have a longitudinal modulus of elasticity that is the same as the transverse modulus of elasticity. For example, an elongated stem made of a homogeneous material or a composite having a uniform construction can have a longitudinal modulus of elasticity that is the same as the transverse modulus of elasticity.

Figure 3:
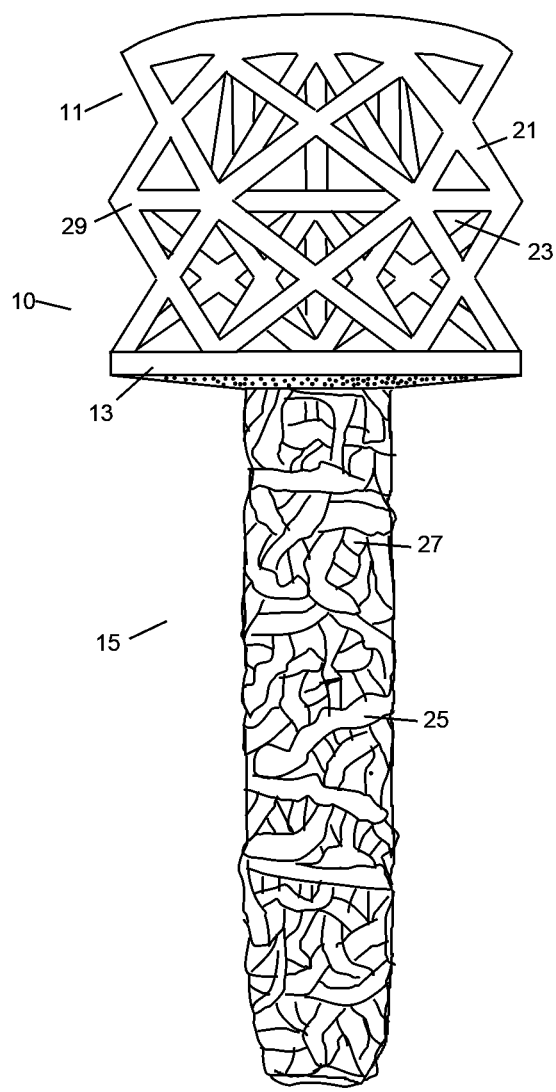
FIG. 3 illustrates a side view of an embodiment of a bone insert.
Figure 4:
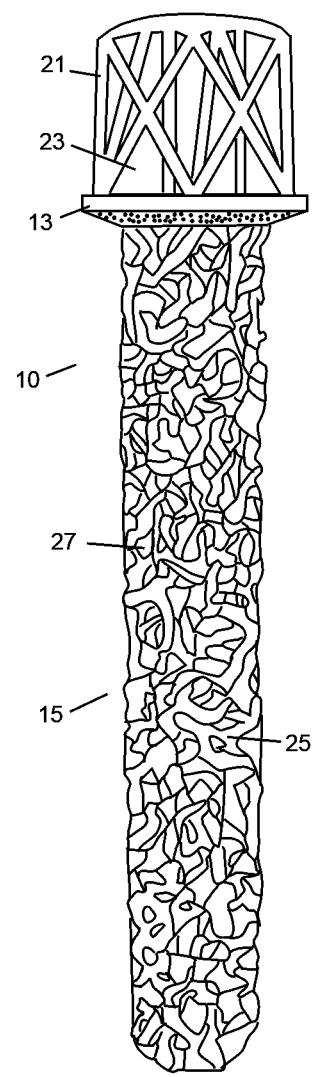
FIG. 4 illustrates a side view of an embodiment of a bone insert.

FIGS. 3-4 illustrate other embodiments of the bone inserts 10. FIG. 3 illustrates a side view of an embodiment of a bone insert 10 that has a cap 11 that is taller and wider than the cap 11 illustrated in FIGS. 1 and 2. In this embodiment, the cap micro struts 21 extend between an upper surface of the cap 11 and a middle layer and the barrier 13. The cap micro struts 21 intersect each other at a center portion 29 of the cap micro struts 21. The height of the cap 11 can provide a different offset from the surface of the bone.

FIG. 4 illustrates an embodiment of a bone insert 10 that has a taller and narrower cap 11 and a longer elongated stem 15 than the bone insert 10 illustrated in FIGS. 1 and 2. In different embodiments, the bone inserts 10 can be made with a variety of different cap 11 heights, different elongated stem 15 lengths and different elongated stem 15 widths. The surgeon can determine the required bone offset and elongated stem length and then select the bone insert that has a cap height and stem length that matches the required bone offset. With reference to Table 2, a group of four different bone inserts 10 that can be available for a surgery. In other embodiments, the different bone inserts 10 can include different cap 11 diameters, cap 11 heights, and stem 15 lengths than the dimensions of the bone inserts 10 listed in TABLE 2.

In TABLE 2, the cap diameters are greater than the stem diameter. However, in some embodiments, the cap diameter can be equal to the stem diameter. The barrier can have a diameter that is greater than or equal to the diameter of the cap and the elongated stem. The stems can have a straight cylindrical portion that can be 5 mm in diameter and a tapered portion that can decrease in diameter from 5 mm to 4 mm.

Figure 5:
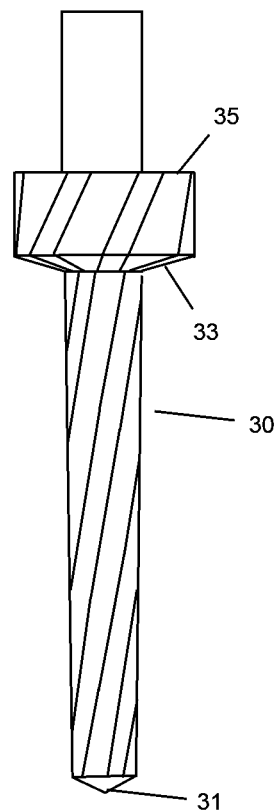
FIG. 5 illustrates a side view of an embodiment of a bone drill bit.
Figure 6:
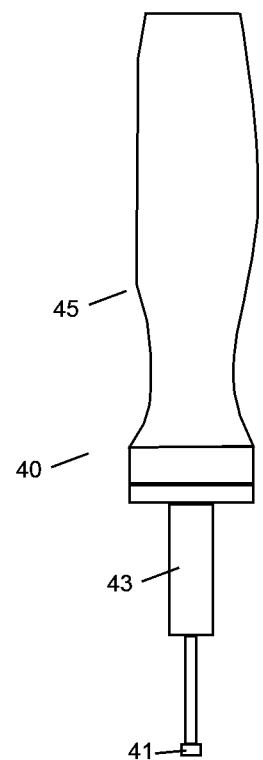
FIG. 6 illustrates a side view of a bone insert insertion tool.
Figure 7:
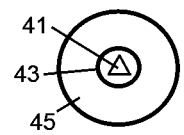
FIG. 7 illustrates an end view of a bone insert insertion tool.

With reference to FIG. 5, a side view of a drill bit 30 is illustrated. The drill bit 30 can be attached to a drill and used to form a hole in a bone that is sized to closely match or be slightly smaller than the outer diameter of the stem of the bone insert. In the illustrated embodiment, the drill bit 30 has a distal end that has a bone cutting tip 31 and a first diameter. At a proximal portion, the drill bit 30 can have a counterbore cutting surface 33 and a stop surface 35. When the drill bit 30 is used to drill a hole in the bone, the drill bit 30 is inserted into the bone until the stop surface 35 is used as a depth guide for the counterbore step surface of the bone. The stop surface 35 functions as a visual cue for the surgeon to accurately set the depth of the step counterbore step surface of the bone. A hole is formed in the bone that has a cross section that matches the side view of the drill bit 30 that has a narrower and longer primary hole and a wider and shorter major hole. The length of the drill bit 30 between the end of the bone cutting tip 31 and the counterbore cutting surface 33 can approximately match the length of the bone insert. Thus, a drill bit 30 for a 10 mm stem height can be much shorter than a drill bit 30 for a 50 mm stem With reference to FIGS. 6 and 7, an example of an embodiment of an insert tool 40 is illustrated. FIG. 6 illustrates a side view and FIG. 7 illustrates a front view of an insert tool 40. The insert tool 40 has a driver tip 41, a shaft 43, and a handle 45. In the illustrated embodiment, the driver tip 41 can have a triangular cross section that can closely fit into a triangular cross section tool recess in the cap of the bone insert such as the cap shown in FIG. 1.

Figure 8:
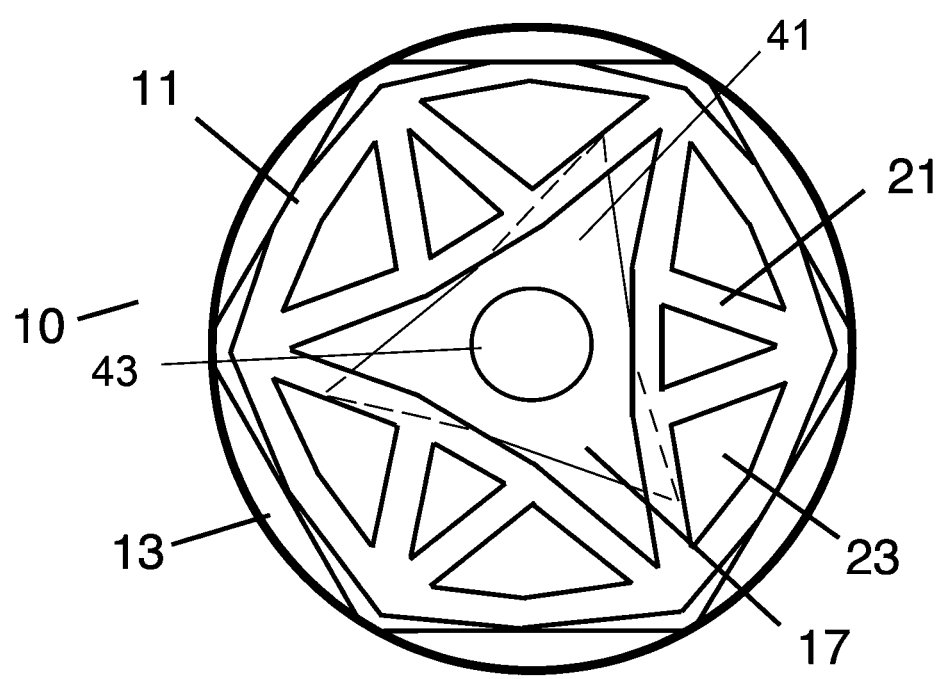
FIG. 8 illustrates a top view of an embodiment of a bone insert with a bone insert insertion tool.

With reference to FIG. 8, the driver tip 41 can be inserted into the tool recess 17 in the cap 11 of the bone insert 10. The end of the driver tip 41 can be pressed against the upper surface of the barrier 13 of the bone insert 10. The surgeon can grasp the handle 45 of the insert tool 40 and use the insert tool 40 to press the bone insert 10 into a drilled hole in the bone until the lower surface of the barrier 13 contacts the bone surface. Alternatively, the insert tool 40 can be used to press the bone insert 10 into a surface of the bone that has not been drilled until the lower surface of the barrier 13 contacts the outer bone surface.

A tapered stem can result in a tighter fit with the host bone as the bone insert is pressed into the bone. This tight fit produces a good initial fixation of the bone insert to the bone. This initial fixation is further improved as the host bone ingrows into the surface features and fenestrations in the stem over the months following the surgery. The strength of the bone can also increase over time as a function of increased force loading on the bone. As discussed above, Wolff's law states that a bone will adapt by becoming stronger if it is placed under higher operating loads. Thus, a bone will become stronger after being exposed to high loads over time.

In some embodiments, the insert tool 40 can have a locking mechanism that can be used to secure the driver tip 41 to the bone insert to allow the insert tool 40 to be used to pull the bone insert out of a bone. For example, by rotating the triangular driver tip 41 within the cap lattice, the corners of the triangular driver tip 41 can be moved under some of the cap micro struts 21. The upper surface of the triangular driver tip 41 can contact the lower surfaces of the cap micro struts 21 and allow the insert tool 40 to pull the bone insert 10 out of the bone.

As discussed above, in some embodiments, the outer surface of the elongated stem of the bone insert can have a helical thread. In these embodiments, the insertion tool can be rotated in a first rotational direction to screw the bone insert into the hole in the bone. The insertion tool can also be rotated in an opposite rotational direction to unscrew the bone insert from the hole in the bone.

In the illustrated embodiments, the driver tip 41 is narrower in width than the cap 11 of the bone insert 10. However, in other embodiments, the driver tip can surround the cap of the bone insert. As illustrated above in FIG. 1, the cross section of the cap 11 can be hexagonal. In some embodiments, the driver tip can have a hexagonal head cross section recess that can closely fit around the hexagonal cap. The bottom edge of the hexagonal head cross section recess can be placed against the barrier to transmit an insertion force from the insert tool 40 to the bone insert.

In some embodiments, the bone insert cap and stem structures can be made of a three-dimensional lattice construction created from many struts that are joined together. The cap micro struts can be coupled in a linear manner. The interdigitation of cement with the porous cap micro struts creates a composite structure that is resistant to fatigue failure or stress crack propagation in multiple planes. The stem micro struts can be coupled in a non-linear manner. The non-linear nature or construction of the struts can provide improved resistance to fatigue failure. In some embodiments, the cap and stem micro struts used to form the bone inserts can be 25-750 microns in diameter. The use of 25-750 micron diameter micro struts can improve the strength to weight ratio of the inserts. The 25-750 micron diameter micro struts lattice structure can also create a bone insert device that can be readily cut with a standard operative sawblade to facilitate extraction of the cemented insert in a revision setting.

In some embodiments, the stem micro struts can have a rough surface finish. The roughness of the individual struts and surfaces increases the surfaces area of the bone inserts to promote bone ingrowth and increases the grip of the insert on surrounding bone when press fit into the bone. The surface roughness can also provide for a more stable initial fixation after insertion into the bone and prior to bone ingrowth. In some embodiments, the surface roughness of the stem micro struts can be created through 3D printers using an electron beam additive manufacturing process.

Trabecular metals can have structural, functional, and physiological properties that are similar to that of bone. Rather than being a solid material, the trabecular metal can have an engineered and interconnected internal pore structure that can support bone fixation and bone ingrowth. In some embodiments, the bone inserts can be made of porous trabecular metal in which either the cap micro struts and/or the stem micro struts are made of a porous trabecular metal. The cap and the stem are secured to opposite sides of a barrier. In some embodiments, porous trabecular metal cap is secured to a porous trabecular metal stem with a barrier design that prevents liquid cement from flowing from the cap to the stem. The barrier can be either a solid barrier or porous with trabeculations that are too small to allow for cement flow to the stem. The porous trabecular metal bone implant can be inserted into a hole in the bone and the barrier can be pressed against the bone. Liquid PMMA cement can then be poured into the cap of the bone implant and the barrier will prevent the liquid PMMA cement from flowing into the stem and the hole in the bone. Bone implants can be made metal materials with a 3D printer as described above or through other processes such as lost wax casting or other suitable fabrication processes.

Figure 9:
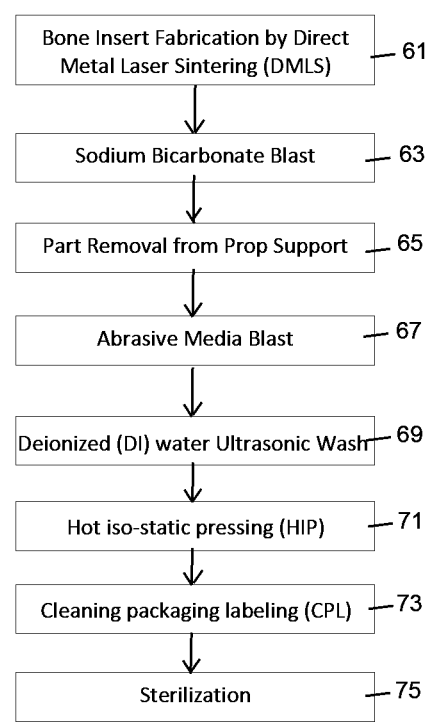
FIG. 9 illustrates a flow chart for fabricating a bone insert.

With reference to FIG. 9, a flowchart for fabricating the bone inserts is illustrated. The bone inserts can be fabricated with a direct metal laser sintering (DMLS) machine 61. The bone inserts can then be coupled to a prop support and blasted with sodium bicarbonate 63. The bone inserts can then be removed from the prop support 65. The individual bone inserts can then be abrasive media blasted 67. The bone inserts can then be placed in a deionized (DI) water ultrasonic wash 69. The bone inserts can then be processed through hot iso-static pressing (HIP) 71. Cleaning packaging labeling (CPL) can be prepared for the bone insert 73. The bone inserts can then be sterilized 75, packaged, and labeled prior to surgical use.

The inventive bone inserts can be used in primary total joint arthroplasty. This process can include drilling into a joint surface with a stepped drill and inserting the bone inserts into the drilled holes. The stepped drill creates a defect that matches the stem and cap of the implant augment. The stepped defect is created to form a defect into which the bone implant augment is placed in zone one. In the primary embodiment, the depth of the defect matches the thickness of the augment cap. In one preferred embodiment, the step drill depth is slightly deeper than the height of the cap. The step drill bit will form a hole that has a step hole that is slightly deeper than the cap. The bone insert can then be pressed into the hole such that the upper surface of the cap can be nearly flush with the surrounding cut joint bone surface adjacent to the hole. When the bone insert is placed in the hole, the cap can be lower than the outer surfaces of the bone that surround the hole in the bone. A small zone of PMMA cement can be placed on the upper surface of the cap. The small zone of PMMA cement will the cure forming a solid structure that will separate the top of the cap from the lower surface of the recessed implant. The small zone of cured PMMA cement can prevent directly physical contact between the cap of the bone insert and the bone implant. The cement on the upper surface of the cap can harden so that metal micro struts on the top portion of the cap are protected from direct physical contact with the metal bone implant.

Standard cementing techniques are then used in which cement is applied to the surface of the host bone and the bone insert. The cement can flow into the porous cap through the fenestrations between the cap micro struts. In different embodiments, the cement can flow in multiple directions through these cap fenestrations. In another embodiment, the larger aperture on the center upper surface of the cap can facilitate the inflow of cement. Because the center aperture is a relatively large opening, more viscous cement types or the cement can be applied at a later time following preparation and mixing of the cement for a more viscous cement which can flow through the fenestrations in the cap. The required quantity of cement can be poured into the cap or can be pressurized manually or mechanically into the cap. After the liquid cement in the cap has cured to a solid, the solid cured cement is interdigitated with the cap to form a composite structure that is stabilized to the surrounding cement mantle and to the host bone and will become more stable as the bone grows into the porous stem portion of the bone insert.

In other embodiments, the step drill bit can product a deeper drilled counterbore to produce a greater volume of cement in the cap and between the cap and the implant. The hole can also be drilled in the bone in which the diameter of the step drill defect for the cap is larger than the diameter of the cap to allow for a larger mantle of cement within the defect surrounding the edges of the cap while the cement also penetrates the cap. The step drill counterbore can alternatively be shallower than the cap thickness such that when the bone insert is placed in the drilled hole, the upper surface of the cap provides a focal location offset from the surrounding host bone surface with the cap rising above the surrounding surface of the bone.

Figure 37:
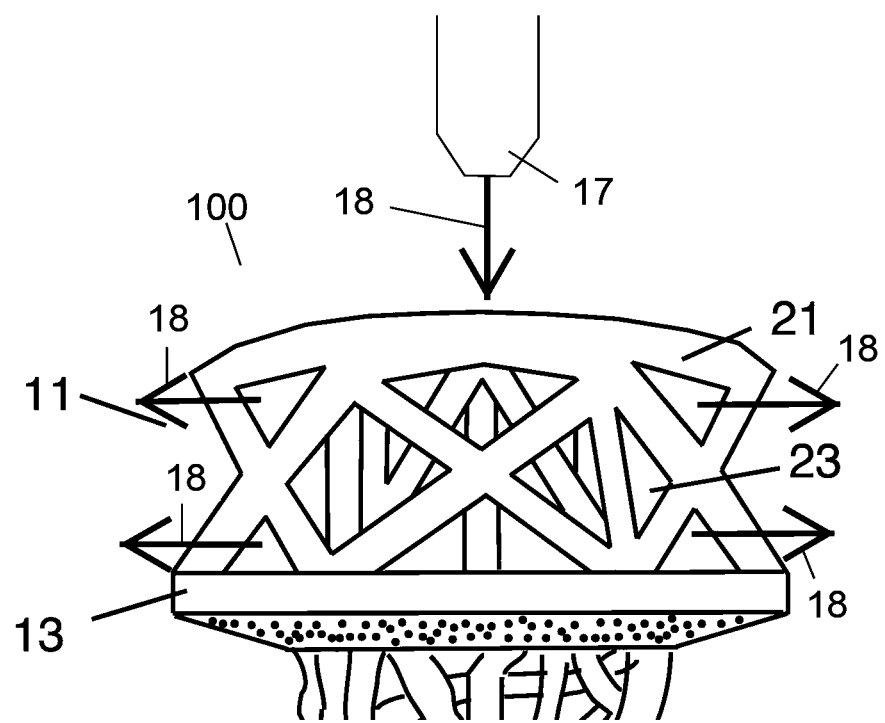
FIG. 37 illustrates a side view of liquid cement flow paths through a bone insert.

This invention describes the novel, highly porous bone insert structure with a high ratio of empty space and fenestrations to metal. The cap portion of the bone insert can have more open empty space than cap micro strut material by volume. This open space in the cap can facilitate the flow of the liquid cement into the cap portion of the bone insert. As discussed above, the cap 11 can have a center insertion tool recess 17 which is larger than the other fenestrations in the cap 11. The cap can have one or more insertion tool recesses that may or may not be centered on the cap. With reference to FIG. 37 in some embodiments, the liquid cement 18 can be applied through a nozzle 17 into the center insertion tool recess 17 in the cap 11 of the bone insert 100. In some embodiments, the nozzle 17 can be placed directly into the center insertion tool recess 17 prior to injecting the liquid cement 18. When liquid cement 18 is injected into the cap 11, the liquid cement 18 can flow through the large open center insertion tool recess 17 and then around the cap micro struts 21 into the adjacent cap fenestrations 23 that are smaller than the center insertion tool recess 17 between the cap micro struts 21. This flow through the cap fenestrations 23 results in a thorough filling of the entire cap volume with the PMMA cement which as discussed improves the strength of the bone implant, bone insert, and host bone assembly. The barrier 13 can be pressed against an outer surface of the bone and prevent the liquid cement 18 from flowing into the hole in the bone and into the stem portion of the bone insert 100. The lattice micro strut 21 structures of the cap 11 and stem can have multiple additional applications for bone filling structures.

In another embodiment, the bone in prepared with a stepped drill to create a countersunk surface in the host bone, the height of which roughly corresponds to the height of the cap of the bone insert device. Cement is placed manually on the bone surfaces and cement is then pressurized manually into the cap while the cement is in liquid form. The fingers of the surgeon may be large enough to seal of the edges of the countersunk hole and after filling the hole with liquid cement, downward pressure into the surface pressurizes the cement into the interstice spaces of cap of the bone insert device.

This invention describes a novel bone insert having a filling lattice structure that is resistant to compression and stem surface features that promote bone ingrowth. This novel lattice structure is designed to match the modulus of bone while also providing properties that facilitate cutting with standard operating room surgical bone saws.

The diameters of the core lattice strut elements can determine how resistant a metal insert structure is to being cut with a saw. By composing the lattice of thin diameter elements, the resistance to cutting is greatly diminished making it much easier to cut than a solid metal implant structure. For example, the interspersing of sub 100 micron diameter cap micro struts creates areas of inherent weakness for cutting that can match the modulus of the cement thus creating a structure that is simultaneously easier to cut and resistant to cement breakdown. Thus, the design of the bone insert can include cut areas across the cap where the expected cuts to the insert are expected. The sub 100 micron diameter areas can be aligned to form planar cut areas. In some embodiments, the height of the caps of the bone inserts can be shortened by cutting across the cross sections of the caps. This easy cutting cap is important in the setting of revision knee surgery when cutting across the cement mantle underneath the bone implant is often required to facilitate removal of the original bone implant prior to installing a revised bone implant. Cutting through the bone inserts is not an important feature for initially securing an original bone implant to the host bone. However, the ability to easily cut through the inventive bone inserts is very important when the original bone implant needs to removed and replaced with a replacement bone implant during bone implant revision surgery.

There are currently no known prior art bone inserts that are used to secure a cemented bone implant interface at a focal point on a convex curved upper surface of a bone insert cap. The only known prior art implant devices that are used to secure a cemented bone interface are cones that are used to secure a cement mantle in the metaphysis. More specifically, no bone insert augments currently exist that are optimized to secure bone cement fixation in zone 1 of total a knee replacement. Zone 1 is at the interface below the implant along the tibial plateau. While the present invention has been described for use with knee replacement surgery, it can also be used for other joint replacement surgeries such as shoulder replacement surgery. Furthermore, no implants have been described that can focally secure the cement fixation along the posterior flanges of the femoral components of total knees, along the distal femoral condylar surfaces, along the anterior femoral flange or along the anterior surface. No known prior art implants have been described that secure the cement mantle and augment the femur in anterior or posterior positions and or flanges that allows upsizing of the femur if over resection or bone loss has occurred in total knee arthroplasty. The combination of securing the cement mantle and augmenting deficient bone at focal locations with minimal point contact with bone implant has not been described in the known prior art for broad used in multiple applications throughout joint arthroplasty including shoulder, elbow, finger, hip, knee and ankle arthroplasties.

There is a great need for bone inserts in joint arthroplasty with ingrowth porous stems with higher porosity caps optimized for securing a cement mantle. No current metal bone insert designs match the modulus of elasticity of the insert to the modulus of elasticity of the underlying bone as well as the modulus of elasticity of the PMMA cement. No current bone insert designs secure the cement with a bone implant device that matches the modulus of the underlying PMMA cement. No current bone insert designs match mechanical properties modulus of elasticity of both the bone and the cement. Existing screws are too rigid and stiff at both the stem component and at the cap relative to the bone and cement which results in weakening and eventual failure.

For all of these reasons, there is a need for bone filling inserts that also can provide a focal offset with rigid fixation prior to cement application that is stable in both shear and tension. Many cemented implants fail in tension at the cement bone interface. No known prior art bone insert currently provides a focal location point of contact for offset of the implant and stabilization of the tensile strength of the bone cement interface with the bone implant.

Screws have been used to augment cement fixation and provide offset for more than three decades and have been a prior standard of care. However, current screws or Kirschner rods are not optimized for matching the elastic modulus of the host bone. Screws and specifically screw heads are also not designed for or capable of complete interdigitation with the cement. The current shapes of the augment screws and Kirschner rods can also create large stress risers that can result in structural failures. The solid or nearly solid screws are also a barrier to removal as they are not easily cut with saws which makes removal of failed or defective bone implants very difficult.

In contrast to the prior art systems, the inventive system has many benefits. The strength of cement used to attach the implant to the host bone can be greatly improved when it is combined with the cap micro struts in the caps of the bone inserts. As discussed, the liquid cement can flow into all fenestrations in the cap of the bone insert and the cement is then cured. The inventive bone insert is part of a final composite structure of rigid cap micro struts oriented in multiple planes in a lattice structure in the cured PMMA cement. Because the cap struts are thin in cross section, they cap micro struts create a large surface area for interdigitation with the PMMA cement that creates a strong mechanical interlock. The combination of cured PMMA cement with the cap micro struts forms a composite structure that resists cracking in multiple planes and is significant stronger than cured PMMA cement alone. This inventive composite structure also results in much greater bonding and physical strength between the cement and the multiplanar cap micro struts in both shear and tensile strength than a solid cap structure because the cement can bind to surface features on the cap micro struts and form a solid structure in the fenestrations between all of the cap micro struts.

The elongated stem can have extreme surface roughness that can provide resistance to pullout from the bone prior to bone ingrowth into the bone implant. Extreme roughness of each beam surface can be an added feature. To create the bone inserts with the desired surface roughness can require digital fabrication using various 3D printer technologies such as: direct metal laser sintering (DMLS), selective laser melting (SLM), electron beam melting (EBM), laser metal deposition (LMD), selective laser sintering (SLS), binder jetting, metal injection molding, and any other known 3D metal fabrication processing machines. The bone inserts can be made of surgical grade metal materials such as titanium, tantalum, or any other suitable metal material. DMLS or other machines can fuse powdered metal media materials together to form the cap, barrier, and elongated stem of the bone insert structures. In an embodiment, the powdered metal media materials can be metals such as titanium. Other technologies such as casting, forging, and machining are not able to create both bone implant diameters nor surface roughness that are desired for press fit characteristics with the surrounding bone to resist pullout and increase surface area for ingrowth. The digital fabrication of the bone inserts can provide increase beam (strut) roughness. The roughness of the bone inserts can be increased with the technique of 3D printing. Multiple techniques can be used to achieve the desired surface roughness of micro struts with minimized diameter. In some embodiments, electron beam processing can be used to create the desired surface roughness.

In other embodiments, the bone inserts can be made of non-metal materials such as polyetheretherketone (PEEK) and polyetherketoneketone (PEKK). The PEEK and PEKK can be provided as a homogeneous filament material which can be 3D printed with a plastic compatible 3D printing machine such as a Fused filament fabrication (FFF), fused deposition modeling (FDM), or other suitable 3D printer machines. Alternatively, the PEEK and PEKK materials can be provided in powdered form that can be used in an SLS 3D printer to fabricate the bone inserts that can include all of the described features and material characteristics.

The process for using the inventive bone inserts can include the steps: cutting a resection surface of a host bone, drilling the cut surface of the host bone with a bone insert drill, placing the bone insert into the drilled hole with the barrier pressed against an exposed surface of the host bone, placing a liquid cement against the cut surface of the host bone, in the cap of the bone insert, and placing the bone implant against the host bone and the bone insert. The barrier of the bone insert is a solid structure that prevents the liquid cement from flowing into the stem portion of the bone insert and drilled hole in the host bone. The liquid cement cures to bond the bone implant to the host bone and the bone insert. Over time, the host bone grows into the fenestrations in the stem of the bone insert to further strengthen the bond of the bone implant to the host bone.

Figure 10:
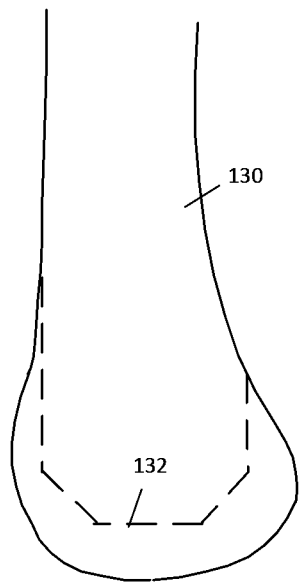
FIG. 10 illustrates a side view of a bone.
Figure 11:
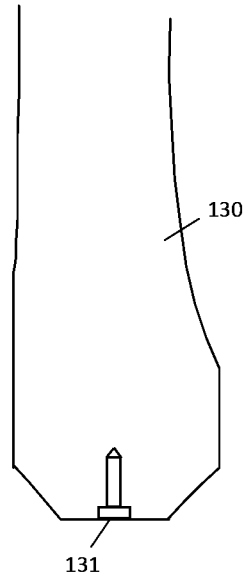
FIG. 11 illustrates a side view of a bone with resectioned surfaces.
Figure 12:
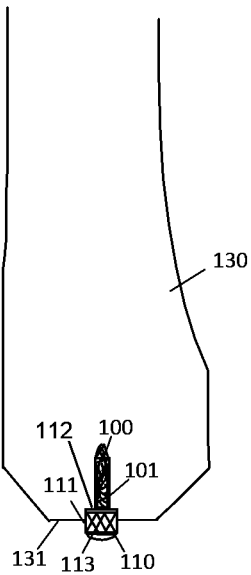
FIG. 12 illustrates a side view of a bone with an embodiment of a bone insert in a distal resection surface.
Figure 13:
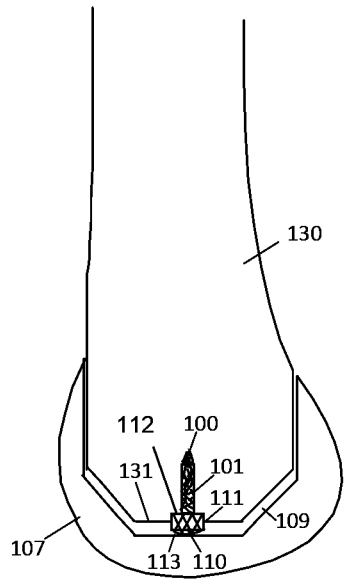
FIG. 13 illustrates a side view of an implant bonded to a bone and a bone insert on a distal resection surface.

FIGS. 10-13 illustrates side views of a femur bone 130 to which a bone implant 107 will be bonded to. With reference to FIG. 10, a bone 130 is illustrated with markings 132 indicating locations of resection cuts. With reference to FIG. 11, the bone 130 has been cut to expose resection surfaces 131 and drilled with the bone insert drill bit. With reference to FIG. 12, bone inserts 100 have been placed in the resection surface 131. The bone inserts 100 includes a cap 110, a barrier 112, and a stem 101 made of a material with surface features which promote bone ingrowth and/or ongrowth. The bone insert 100 has been fully inserted into the bone 130 so that the barrier 112 is in direct physical contact with the resection surface 131. With reference to FIG. 13, the implant 107 is placed on the bone 130 with the barrier 112 against the bone 130. A surface of the implant 107 is in direct physical contact with a top surface 113 of the cap 110. It can be undesirable to have directed metal to metal contact particularly if the metals that are in contact are not the same types of metal. When different metals contact each other, galvanic corrosion can occur or direct abrasive wear. In some embodiments, the exposed outer facing surfaces of the caps can be coated with cured PMMA that can prevent the metal bone implant from directly contacting the metal bone insert. In other embodiments, the cap micro struts in the cap can be designed to minimize contact surface area of the cap with the implant both at contact surface and below the contact surface of the cap. This can result in much less wear at the contact areas compared to solid metal caps in which wear exposes the implant to increasing volume of metal. This invention also describes a small cured PMMA spacer that can be applied to the top of the cap to prevent direct metal on metal contact when the insert is used as an augment when preferred by the surgeon.

Liquid PMMA cement 109 can be applied to the exposed bone 130, the cap 110 of the bone insert 100 and the implant 107. The liquid PMMA cement 109 can flow into the fenestrations in the cap 110 of the bone inserts 100. However, the barrier 112 of the bone insert 100 into the space between the implant 107 and the bone 130. The barrier 112 can prevent the PMMA cement 109 from flowing into the stem 101 portion of the bone insert 100. The liquid PMMA cement 109 can cure and chemically bond to the cap 110 of the bone insert 100 and create a strong mechanical bond between the implant 107 and the bone 130. In an embodiment, the cap micro-struts of the cap 110 can be textured or have physical features such as grooves, holes, fenestrations, etc. which can improve the interdigitation of the liquid PMMA cement with the implant 107. The barrier 112 can prevent the liquid cement from flowing into the space between the stem 101 and the inner diameter of the hole in the bone. The bone can ingrow into the fenestrations in the stem 101 of the bone insert 100 and ongrowth onto the surfaces of the stem micro-struts.

Figure 14:
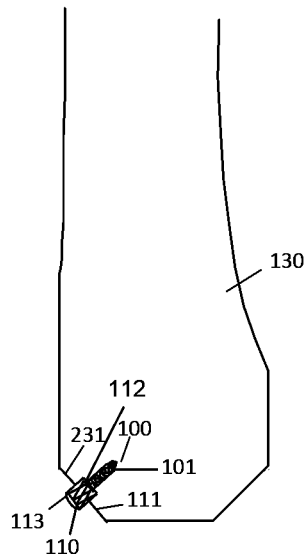
FIG. 14 illustrates a side of view of a bone with an embodiment of a bone insert in an anterior resection surface.
Figure 15:
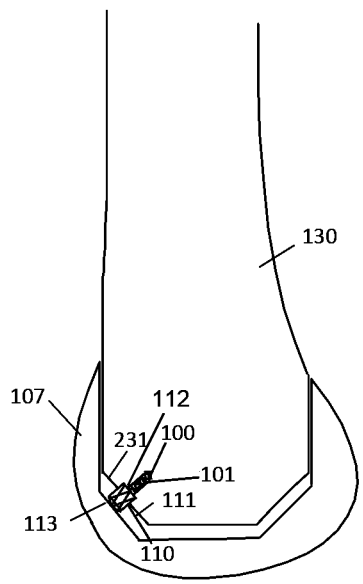
FIG. 15 illustrates a side view of an implant bonded to a bone and a bone insert on an anterior resection surface.

In other embodiments, the bone insert 100 can be inserted into a different resection surface such as an anterior resection surface. With reference to FIG. 14, bone inserts 100 have been placed in the anterior resection surface 231. In this embodiment, the bone insert 100 includes a cap 110, a barrier 112, and a stem 101 made of a material with surface features which promote bone ingrowth and/or ongrowth. The bone inserts 100 have been fully inserted into the bone 130 so that the barrier 112 is in direct physical contact with the anterior chamfer resection surface 131. With reference to FIG. 15, the implant 107 is placed on the bone 130 with a surface of the implant 107 in direct physical contact with a top surface 113 of the cap 110 which is opposite the first surface 111. In other embodiments, the bone insert 100 can be placed on any surface of the bone 130 between the bone 130 and the implant 107.

The insertion of the bone insert 100 into the bone 130 can comprise various procedural steps. In an embodiment, the bone resection surface can be drilled with the bone insert drill bit and the stem 101 of the bone insert 100 can be placed into the hole formed until the barrier 112 is pressed against a surface of the bone 130 to prevent liquid cement from flowing into the stem 101 portion of the bone insert 100. The drill can be a stepped or counterbore drill bit which creates an insert hole having a specific depth and diameter.

In other embodiments, the bone insert 100 can be physically pressed into the bone 130. The force of the stem 101 against the bone 130 can create the hole in the bone 130. The surgeon can then trial the focal offset of the bone insert 100 to determine the proper focal offset of the bone insert 100. If the bone insert 100 needs to be replaced, the bone insert 100 can be removed and a replacement bone insert 100 can be pressed into the same hole formed by the previously trialed bone insert 100. The bone inserts 100 can have caps 110 that have cap micro-strut surfaces and structural features that can allow the surgeon to easily remove the bone insert 100 with a bone insert tool that can be used to grasp and/or pull the cap 110 and bone insert 100 away from the bone 130. The bone insert 100 can also have a barrier 112 that can be pressed against the bone 130 to prevent liquid cement from flowing into the stem portion and the hole drilled in the bone 130.

The inventive process can solve a significant problem that occurs when too much bone is removed during resectioning. There are no preferred methods for easily adding bone material to the cut bone surfaces other than using a standard screw with its aforementioned limitations. Augmenting the bone to readjusting the intended position of the bone implants on host bone to compensate for cuts in which too much bone has been removed, can be very difficult without a reliable solution especially in the setting of primary total joints in which specialized bone implants are not available. These specialized implants for revision surgery allow for solid metal augments to be screwed into the specialized implants to produce thicker metal constructs in specific locations. The assembled implants with secured augments are cemented into host bone with the solid metal augments used to fill the bone void. Augments in these revision implants can only be secured in locations in which screw holes have been placed in the undersurface of the implant and typically these locations are either the distal femur or posterior flange of the implant. These implants do not allow for focal adjustments at any location of the surgeon's choice and provide limited ability to make adjustments in multiple planes. The application of the described bone inserts solves this problem by allowing surgeons to easily adjust the bone implant offset at any location and has the added benefit of providing a stronger bond between the bone and bone implant because the bone implants can be secured to bone inserts that are mechanically bonded in holes in the bone. The caps of the bone inserts are completely infused with the liquid cement which strengthens and improves the stabilization of the cured cement. The caps of the bone inserts also provide a small focal area of contact or no direct physical contact with the bone implant which minimizes metal to metal contact wear. The bone inserts offer the added benefit of allowing the surgeon to place the inserts into the host bone and trial bone implants placed on the inserts to determine correct adjustment of the component alignment. The inserts then can be readjusted until the proper position of trial implants is obtained. Once the proper position of the inserts is achieved, the cement can be mixed, applied to the inserts and bone surfaces and final bone implants placed.

In contrast, a standard prior art bone implant may only rely upon PMMA cement placed on the outer surfaces of the bone to provide the mechanical bonding to the bone implant. This includes situations in which augments are applied to revision implants. The mechanical strength of the cured PMMA cement is much weaker than a cured PMMA cement that is reinforced with a metal lattice. The mechanical coupling of the cured PMMA cement to the host bone is also weaker than cured PMMA cement that is rigidly coupled to the cap of the bone insert that has a stem that is in a hole in the bone where the bone is ingrown into the stem of the bone insert.

Figure 16:
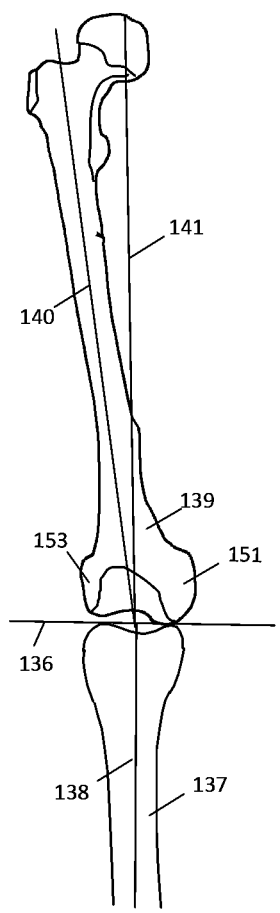
FIG. 16 illustrates an anterior view of a femur and tibia.

The alignment of the implant for total knees can be variable with both mechanical alignment and kinematic alignment being used broadly. The need for the alignment adjustment of the implant may need to be adjusted based on the discretion of the surgeon. With reference to FIG. 16, an anterior view of the knee joint is illustrated. The distal surfaces of the femur 137 can be a horizontal axis that is parallel to the rotational axis of the knee 136. Each patient's anatomical geometry can be different and the femur 139 can have various alignment configurations with the tibia 138. In the illustrated example, the geometric axis 141 of the tibia 138 can be defined by a line between the head at the proximal end of the femur 139 and the center of the knee. The geometric axis 141 can be perpendicular to the rotational axis of the knee 136 and aligned with the center axis of the tibia 138. As illustrated, the anatomic center axis 140 of the femur 139 is angled from the geometric center axis 141 of the tibia 138 and is not be perpendicular to the rotational axis of the knee 136 in the illustrated example. However, in other embodiments (not illustrated) the surgeon may configure the patient's leg with the anatomical axis 140 of the femur 139 in a perpendicular orientation relative to the rotational axis 136 of the knee and aligned with the center axis 138 of the tibia 137.

Figure 17:
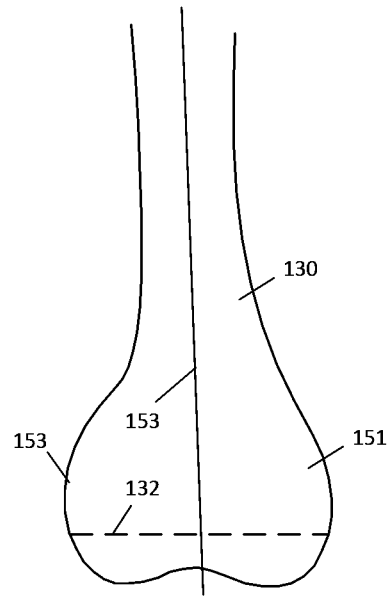
FIG. 17 illustrates an anterior view of a distal portion of a femur.
Figure 18:
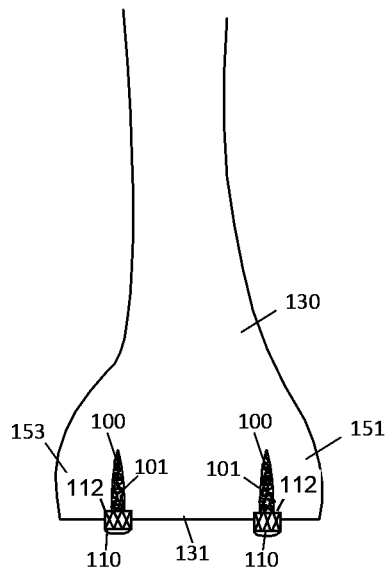
FIG. 18 illustrates an anterior view of a femur with a distal resection surface with bone insert.

FIGS. 17-20 illustrate anterior view of a femur bone 130 and bone implant 107. With reference to FIG. 17, the bone 130 is illustrated with a lateral condyle of the femur (LFC) 153 and a medial condyle of the femur (MFC) 151. The resection cut markings 132 extends through portions of both the LFC 153 and the MFC 151. The resection cut markings 132 may not be perpendicular to the center axis of the femur 153. FIG. 18 illustrates the bone 130 after being cut with a resection surface 131 and with bone inserts 100 placed in the resection surface 131 on the LFC 153 and MFC 151. The bone inserts 100 have been fully inserted into the bone 130 so that barriers 112 are in direct physical contact with the resection surface 131 of the bone 130. As discussed, the barriers 112 can prevent liquid PMMA from flowing into the stem portions of the bone inserts 100 and the holes in the bone 130. The implant 107 is placed on the bone 130 and in direct physical contact with the top surfaces of the caps 110.

Figure 19:
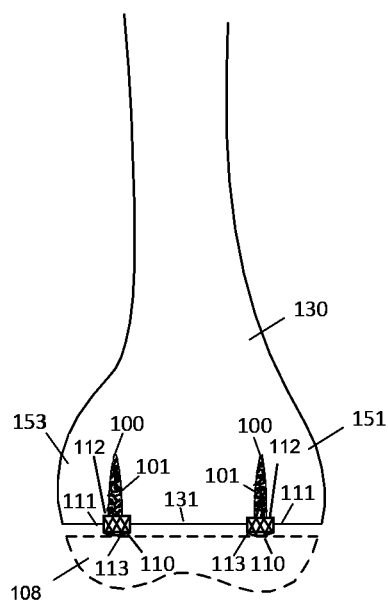
FIG. 19 illustrates an anterior view of a femur with a distal resection surface with bone insert with a trial implant.

With reference to FIG. 19, the surgeon can check or test the augment offset of the implant 107 provided by the bone insert 100 relative to the bone 130 and determine if the offset is correct. Checking the offset can include length and angular offset measurements of a trial implant 108 relative to the bone 130. Checking can also be performed for functional performance with use of trial implants 108 and range of motion of the joint with assessment of stability and motion. For example, the offset of the bone implant 107 can be tested for proper joint balance that has the proper articulation and ligamentous balance in all orientations of the joint.

If changes need to be made, the balance of the bone implant 107 can be revised with another trial using different bone inserts 100. The bone inserts 100 that did not have the correct offset can be removed and replaced with other bone inserts 100 that have caps 110 having different thicknesses to change the offset length or change the angle between the resection surface 131 and the trail implant 108. The position of the trial implant 108 and various mechanical tests can be performed to determine if the final implant will be properly positioned by the bone inserts 100. It is also possible to fine tune the amount of offset with step drilling to a deeper depth. If the offset is too long, then the bone inserts 100 can be removed and the step drill can be used to adjust the depth of the step drill hole to the correct length.

Figure 20:
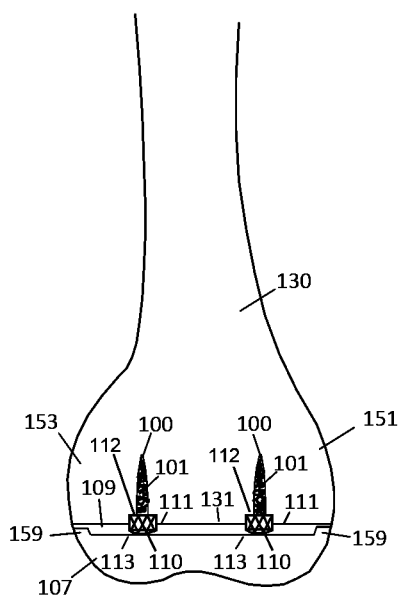
FIG. 20 illustrates an anterior view of a femur with a distal resection surface with bone inserts bonded to a final implant.

With reference to FIG. 20, once the correctly sized bone inserts 100 and step drill depth are found to properly position the implant 107, liquid PMMA 109 can be applied to the caps 110 of the bone inserts 100, the resection surface 131 of the bone 130, and the bonding surface of the implant 107. The barriers 112 of the bone inserts 100 can prevent the liquid PMMA from flowing into the stem portions 101 of the bone inserts 100 and the hole in the bone 130. The bone 130 can ingrow into the fenestrations in the stems 101 and ongrow onto the exposed surfaces of the stems 101. The liquid PMMA can cure to bond the implant 107 to the bone 130 and caps 110 of the bone inserts 100. In the illustrated embodiment, the implant 107 can include a raised edge 159 which can extend around the outer perimeter of the implant 107. The raised edge 159 can function to help retain the liquid PMMA cement 109 within the space between the bone 130 and the implant 107. The height of the raised edge 159 can be less than the thickness of the caps 110 of the bone inserts 100 so that the implant 107 will contact the bone inserts 100 but the raised edge 159 will not contact the bone 130. The inventive bone inserts 100 can provide bone implant 107 offsets at virtually any location resection surface 131 on the bone 130 and greatly improves the stability of the cured cement on the bone 130.

Figure 21:
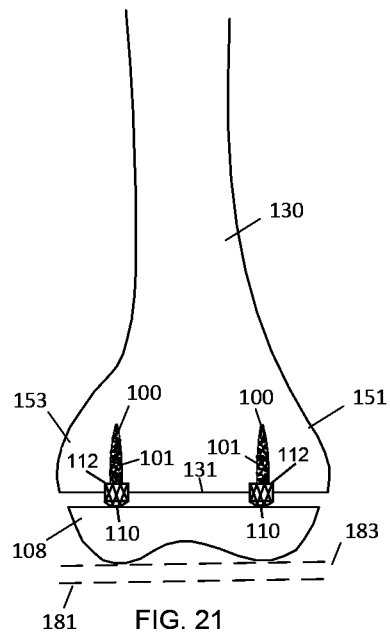
FIG. 21 illustrates an anterior view of a femur with a distal resection surface with a trial implant.
Figure 22:
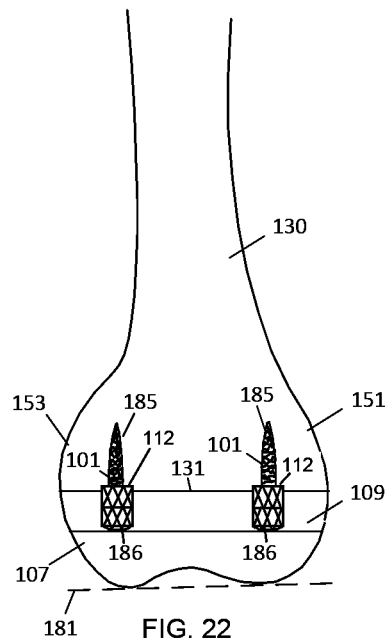
FIG. 22 illustrates an anterior view of a femur with a distal resection surface with bone inserts.

FIGS. 21-24 illustrate a process for adjusting the cap thicknesses of the inserts to properly offset the implant. With reference to FIG. 21, the proper predetermined length offset of the implant 107 relative to the bone 130 can be represented by line 181. However, in the illustrated embodiment, a trial implant 108 is measured, calculated or trialed to determine the offset of the implant. In this example, the measured offset line 183 is substantially shorter than the proper offset line 181. The offset line 183 can be determined during a trial process of the inserts 100 where a trial implant is placed on the inserts 100 and the stability and range of motion can be tested. If these trial implant 108 tests fail, the surgeon can make corrective adjustments to the caps of the inserts 100 to alter the offset so the final implant will match the offset line 183. With reference to FIG. 22, the length of the offset between the bone 130 and the implant 107 has been altered by replacing the inserts 100 with replacement inserts 185 that have thicker caps 186. With the replacement inserts 185, the offset of the final implant 107 matches the proper predetermined length offset line 181. If the offset position of the implant needs to be shortened, the inserts 100 can be replaced with inserts 100 having thinner caps. In this embodiment, the angle of the resection surface 131 was correct, so the thicker caps 186 of the inserts 185 can have the same thickness so that the angle of the implant 107 is not changed relative to the bone 130.

Once the proper bone inserts 100 are inserted into the bone, the barriers of the bone inserts 100 can be pressed against the outer surface of the bone 130. Liquid PMMA 109 can be applied to the exposed areas of the bone 130, the caps 186 of the replacement inserts 185 and the bonding surface of the final implant 107. The liquid PMMA 109 can cure to chemically bond to the caps 186 of the bone inserts 185 and mechanically bond the implant 107 to the bone 130. The barriers 112 can prevent liquid PMMA 109 from flowing into the holes in the bones 130 and the stem portions 101 of the bone inserts 185 so that the bone 130 can ingrow into the fenestrations in the stem and/or ongrow onto the contact surfaces of the stem of the bone inserts 185.

Figure 23:
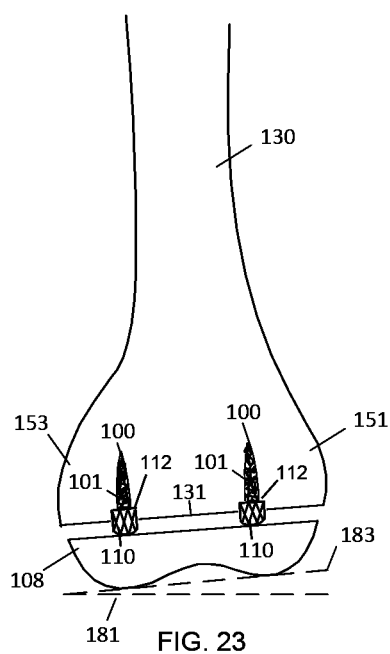
FIG. 23 illustrates an anterior view of a femur with a distal resection surface with bone inserts and a trial implant.
Figure 24:
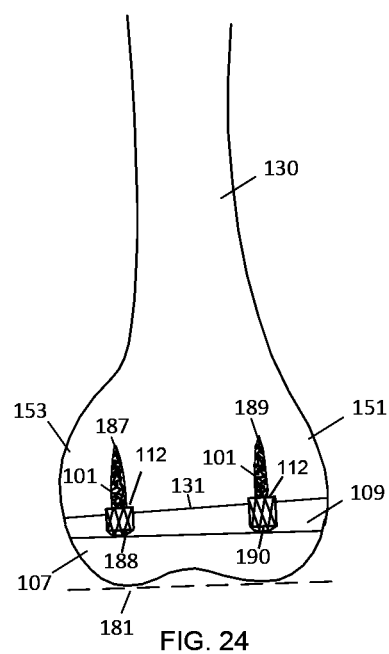
FIG. 24 illustrates an anterior view of a femur with a distal resection surface with bone inserts bonded to a final implant.

With reference to FIG. 23, an embodiment is illustrated where the bone inserts 100 are used with a trial implant 108. The trial implant 108 is then measured, calculated or trialed to determine a trial offset line 183. In this example, the trial offset line 183 is at a different angle than the proper offset line 181 and an adjustment to the bone inserts 100 will need to be made. The offset angle of the trial implant 108 relative to the bone 130 can be changed and corrected by using bone inserts 100 having different thickness caps 110. With reference to FIG. 24, the original bone inserts 100 have been removed and replaced with a first bone insert 187 which has a thick cap 188 in the LFC and a second bone insert 189 which has a thicker cap 190 in the MFC. These replacement bone inserts 187, 189 can cause the final implant 107 offset to be properly angled and positioned and match the correct predetermined offset line 181. FIGS. 23 and 24 illustrate one embodiment of an angular correction. However, if the surgeon needs to angle the implant 107 more towards the medial side, the bone insert 100 placed in the MFC 151 can have a thinner cap 110 than the cap 110 on the insert 100 placed in the LFC 153. The use of multiple bone inserts 100 can provide greater stability between the bone implant 107 and the bone 130.

Once the surgeon determines that the selected bone inserts 100 will provide the proper offset of the implant 107 relative to the bone 130 by a trial process, the barriers of the bone inserts can be placed against surfaces of the bone 130. A liquid PMMA cement 109 can be applied to the caps 188, 189 of the bone inserts 100, the exposed resection surface 131 of the bone 130, and the bonding surfaces of the implant 107. The liquid PMMA cement 109 may also injected or placed in the spaces between the bone 130 and the implant 107 around the cap 110. The barrier 112 can prevent the liquid PMMA cement 109 from contacting areas between the bone 130 and the stem portions of the inserts 100. The liquid PMMA cement will harden into a solid and chemically bond to the cap micro struts of the caps 188, 190 of the bone inserts 100 and mechanically bond the bone 130 to the implant 107. The stems 101 can have bone ingrowth and ongrowth surfaces which provide interdigitation surfaces with the bone. Once cured and fully hardened and bone has grown into the stems 101 of the inserts 100, the implant 107 will be rigidly attached to the bone 130.

Figure 25:
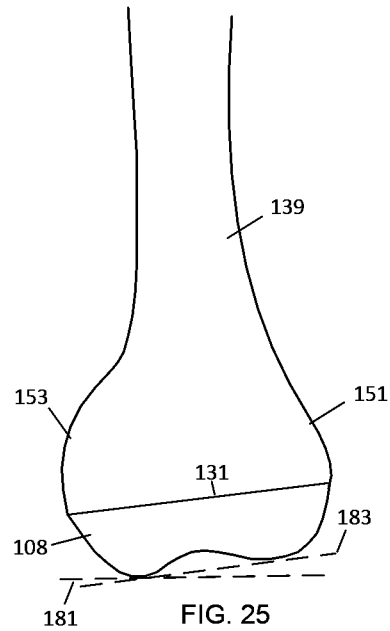
FIG. 25 illustrates an anterior view of a femur with a distal resection surface with a trial implant.
Figure 26:
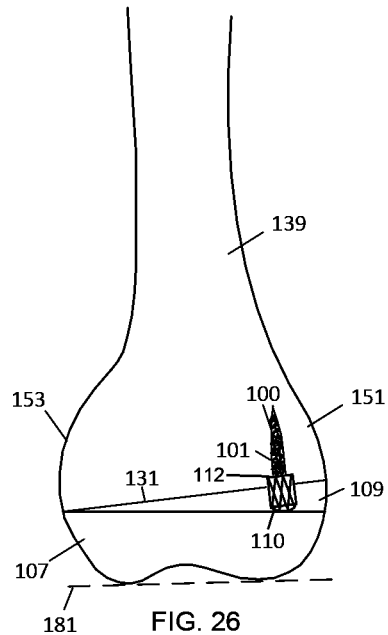
FIG. 26 illustrates an anterior view of a femur with a distal resection surface with a bone insert bonded to a final implant.

In some embodiments is can be possible to make angular corrections to the offset of the implant with a single implant. FIG. 25 illustrates a femur 139 with a resection surface 131. A trial implant 108 can be placed on the resection surface 131 and the surgeon can perform a trial process and determine that the measured offset line 183 does not match the correct offset line 181 and material needs to be added to the MFC 151 side of the resection surface 131. With reference to FIG. 26, a stem 101 of the bone insert 100 is inserted into the MFC 151 side of the resection surface 131 and the trial process can be repeated. In this example, the trial process is passed and liquid PMMA 109 can be applied to the resection surface 131, the cap 110 of the bone insert 100 and the implant 107 to mechanically bond the implant 107 to the femur 139. Again, the barrier 112 can prevent the liquid cement from entering the drilled hole in the bone and the stem 101 of the bone insert 100.

Figure 27:
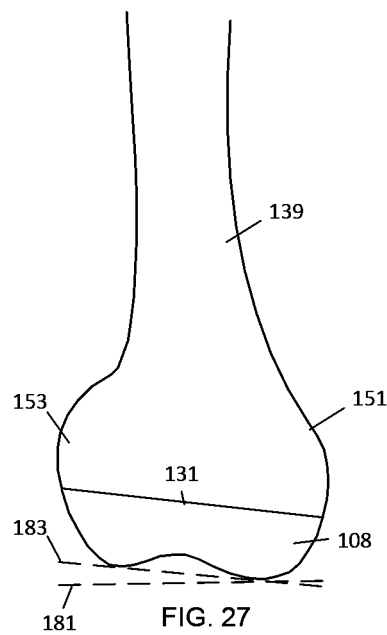
FIG. 27 illustrates an anterior view of a femur with a distal resection surface with a trial implant.
Figure 28:
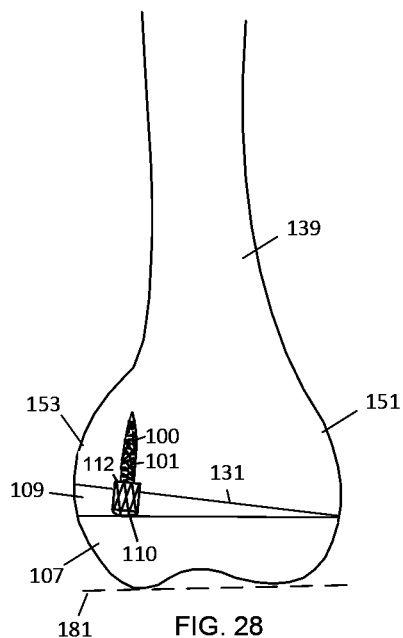
FIG. 28 illustrates an anterior view of a femur with a distal resection surface with a bone insert bonded to a final implant.

With reference to FIG. 27, a trial implant 108 is attached to the resection surface 131 and the trial process can determine that material needs to be added to the LFC 153 side of the resection surface. With reference to FIG. 28, a bone insert 100 is inserted into the LFC 153 side of the resection surface 131 to correct the offset of the implant 107. When the trial testing has been passed, liquid PMMA 109 can be applied to the resection surface 131, the exposed PMMA portions of the insert 100 and the cap 110 of the implant 107 to mechanically bond the implant 107 to the femur 139. The barrier 112 can prevent the liquid PMMA 109 from flowing into the stem portion 101 of the bone insert 100 and the hole in the femur 139

Figure 29:
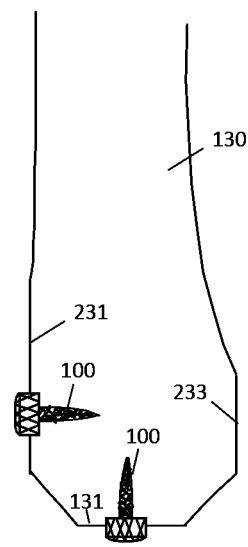
FIG. 29 illustrates a side view of a bone with bone inserts in anterior and distal resection surfaces.
Figure 30:
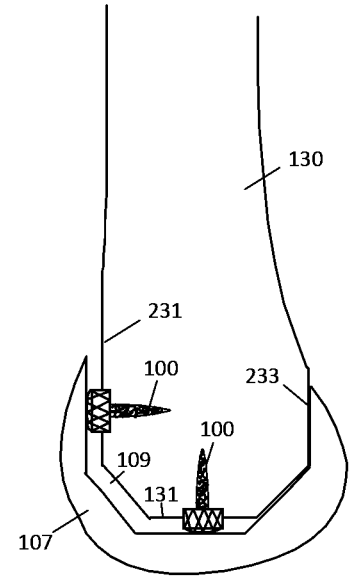
FIG. 30 illustrates a side view of a bone with bone inserts in anterior and distal resection surfaces bonded to a final insert.

With reference to FIGS. 29-32, side views of a bone 130 having multiple resection surfaces 131 are illustrated. In some embodiments, the bone inserts 100 can be placed on multiple resection surfaces 131 which are not in the same plane. The bone inserts 100 can allow the surgeon to move the implant 107 towards the anterior or posterior sides of the bone 130. With reference to FIG. 29, one or more bone inserts 100 are placed in an anterior resection surface 231 and a distal surface 131 that can be perpendicular to a center axis of the bone 130 With reference to FIG. 30, the implant 107 position relative to the bone 130 can be adjusted towards the anterior surface by placing tack inserts 100 in an anterior resection surface 231. Multiple bone inserts 100 can allow for greater stability and more complex adjustments between the bone implant 107 and the bone 130.

Figure 31:
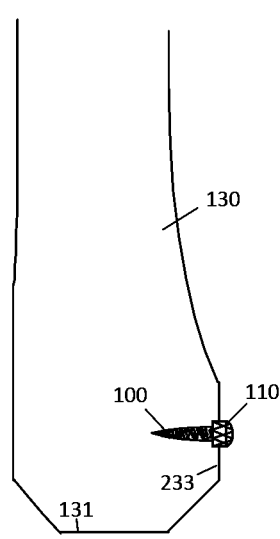
FIG. 31 illustrates a side view of a bone with a bone insert in a posterior resection surface.
Figure 32:
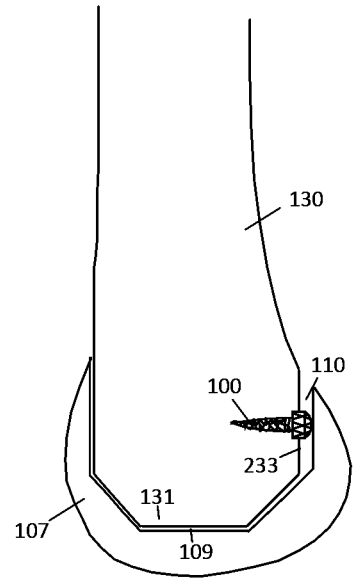
FIG. 32 illustrates a side view of a bone with a bone insert in a posterior resection surface bonded to a final insert.

With reference to FIG. 31, one or more bone inserts 100 are placed in a posterior resection surface 233 of the bone 130 that can be substantially parallel to a center axis of the bone 130. With reference to FIG. 32, the implant 107 is moved towards the posterior surface relative to the bone 130 by using bone inserts 100 that have different offsets in the posterior surfaces 233. By having bone inserts 100 in multiple resection surfaces the surgeon can have more precise control of the position of the implant 107 relative to the bone 130 to match the predetermined required offset distances, relative positions and angles in three dimensional space. Placement of bone inserts 100 in the posterior resection surface 233 can allow the surgeon to securely increase the size of a femoral component to reduce a selective flexion gap imbalance.

The present invention illustrates how an implant can be offset relative to a bone in different directions in three-dimensional space. In an embodiment, the bone can be aligned with an X, Y, and Z coordinate system with the center axis of the bone aligned with the Z-axis. The anterior surface can face the X-axis and the joint at the distal end of the bone can rotate about the Y-axis.

Figure 33:
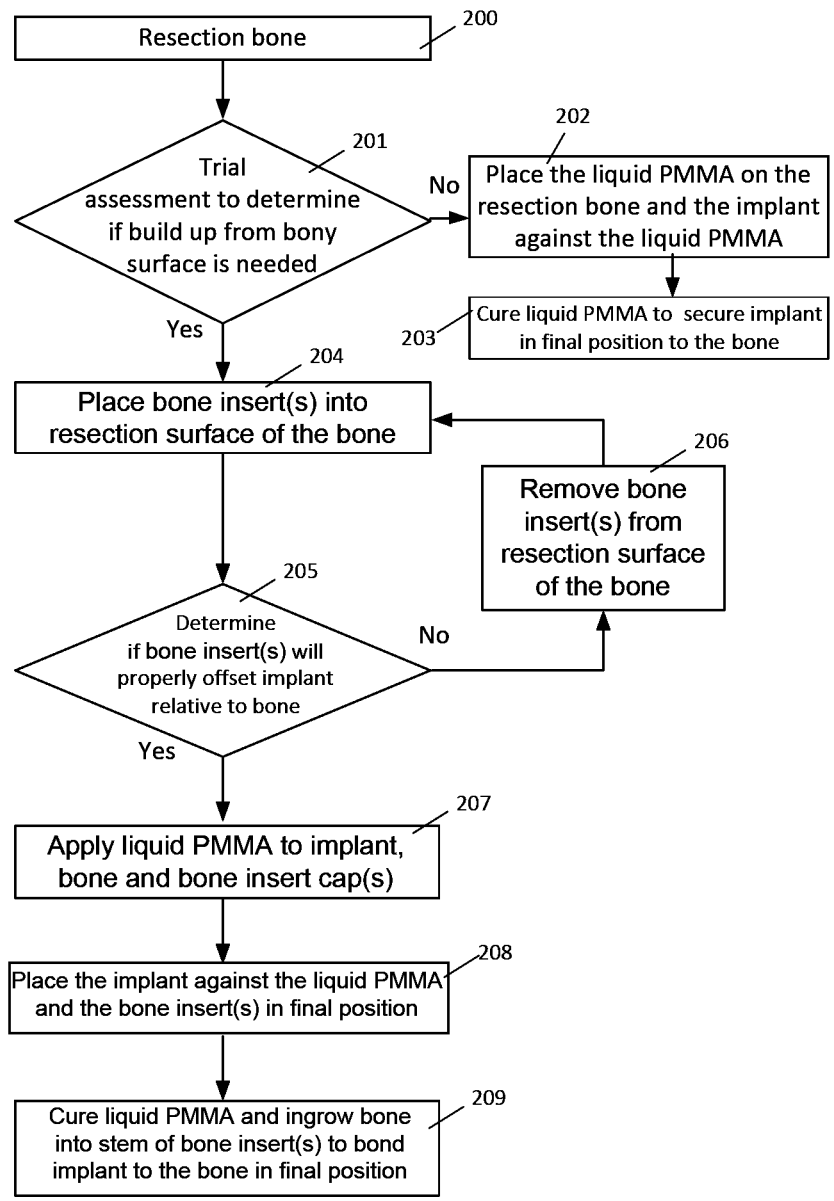
FIG. 33 illustrates a flow chart for adjusting bone inserts and bonding a final implant to a bone and the bone inserts.

FIG. 33 is an example flow chart describing the steps used to attach implants to a resectioned bone. A bone is first resectioned 200. Trialing is then performed to determine if the implant will be properly positioned relative to the bone or if build up from the bony surface is needed 201. The trialing can be a test of the resection to determine if the position is correct. The trialing can depend upon the type of joint being repaired and can involve joint motion testing. The trialing will be described in more detail later. If the resection bone is proper and no build up from the bony surface is needed, liquid PMMA can be placed on the resection bone and the implant can be placed on the liquid PMMA and the bone 202. The liquid PMMA can then cure to secure the implant in the final position on the bone 203. If build up of the bony surface or an offset is needed, one or more bone inserts are placed into a resection surface of the bone 204. The surgeon can then determine if the one or more bone inserts will provide the proper offset 205. In some embodiments, a surgeon can use a tool such as a gauge to check the offset of the implant relative to the bone. In other embodiments, the implant can be placed against the inserts to determine the offset of the implant relative to the bone. The implant placed against the insert can be trialed for range of motion and stability to determine clinical adequacy of the correction of the implant relative to the bone. Alternatively, any other measuring method can be used to determine the offsets of the bone inserts. If an offset error is determined, the bone inserts can be removed from the resection surface of the bone 206 and bone inserts that provide different offsets are inserted into the resection surface of the bone 204.

In an embodiment, the surgeon can have a number of bone inserts that have different offset sizes. For example, the different bone inserts can be sized in 1 mm or other dimensional increments. In use, the user can insert the stem of the bone inserts and determine that the offset is the wrong length and then find a proper length offset insert based upon trial and error. In an embodiment, a surgeon can use a kit of paired inserts that can include various length offsets. In an embodiment, the bone inserts can be clearly marked so that the surgeon will know the different offsets of the different bone insert sizes which can improve the efficiency of the described procedures. The offsets of the bone inserts in a kit can range from 1 mm-15 mm in 1 mm increments or any other suitable range of distances and increments. Thus, there can be 15 or more bone inserts each having a different offset distance. For example, the bone inserts can have dot markings that indicate the offset distance with each dot indicating an additional 1 mm offset. In other embodiments, the bone inserts can be numerically marked or color coded based upon the offset distance.

If the bone inserts provide the proper implant offset relative to the bone, liquid PMMA cement can be applied to the bone inserts, bone and implant 207. The implant is placed against the liquid PMMA which fills all gaps between the resection surface of the bone and the implant 208. In some embodiments, the liquid PMMA can be applied with a tool such as a brush or spatula to the contact surfaces of the stem sections with the insert and the implant. Liquid PMMA can also be injected with a tool such as a liquid PMMA injection gun through a nozzle into a gap between the resection surface of the bone and the implant to fill this space. Thus, the liquid PMMA can be applied to the bone inserts, bone and implant in various different ways. The liquid PMMA fills this space, cures and hardens to bond to the cured PMMA portions of the bone inserts on the first and second resection surfaces. The bonding of the liquid PMMA to the cured PMMA portions of the bone inserts create a high strength mechanical connection between the bone and the implant 209.

The use of inserts provides several benefits. The bone inserts provide a means for correcting resection errors when excess bone material has been removed. The physical strength of the PMMA connection to the bone is also improved because the stem portions of the bone inserts penetrate into the bone and the barriers prevent the liquid PMMA from flowing into the stem or hole in the bone. The stems and fenestrations of the bone inserts provide ongrowth and ingrowth surfaces resulting in a stronger connection than that provided by liquid PMMA and bone interdigitation surfaces of the bone inserts. The liquid PMMA cures around the micro-struts of the caps of the bone inserts to form a solid metal lattice and PMMA cement composite structure having very high mechanical properties such as tensile, compression and shear strengths. The strength of the lattice and PMMA cement composite structure can be uniform or nearly uniform across the width and height of the cured liquid PMMA and cap portions of the bone inserts.

Figure 35:
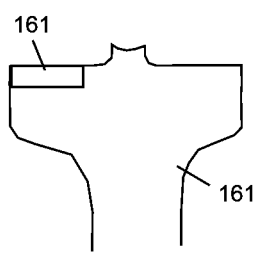
FIG. 35 illustrates a side view of a host bone and a PMMA bone reconstruction.

The inventive bone insert and method can also provide improvements for revisions of PMMA secured bone implants that have failed. With reference to FIG. 35, a side view of a host bone 161 and a PMMA bone reconstruction is illustrated. In this case, a portion of the host bone has suffered bone loss which has been cut from the bone and replaced with PMMA 163 which has cured to provide replacement bone material. In joint arthroplasty, liquid PMMA cement rarely penetrates more than several millimeters into boney surfaces. Because the PMMA is not strengthened it has failed and needs to be replaced with a metal bone implant. To prepare the bone for revision surgery, the cured PMMA 163 must be removed and another portion of the bone 161 is cut creating a resection surface.

Figure 36:
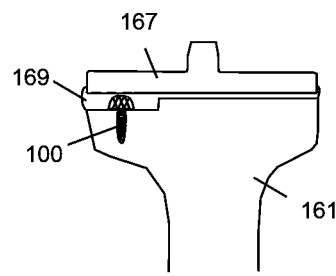
FIG. 36 illustrates a side view of a host bone, a bone implant reconstruction using a bone insert.

FIG. 36, a side view of a host bone 161 after revision surgery is illustrated. A bone insert 100 has been installed with the stem of the bone insert pressed into the bone 161 and the barrier of the bone insert pressed against the exposed outer surface of the bone 161. The convex outer surface of the cap of the bone insert contacts the lower surface of the bone implant 167 at a focal point contact area. Liquid PMMA cement has been applied to the cap portion of the bone insert and the surface of the bone 161 adjacent to the bone implant 167. The resulting construct of cured PMMA cement 169 that is strengthened by the metal lattice of cap micro struts and the stem that is rigidly bonded to the bone with mechanical coupling and bone ingrowth into the stem. The mechanical strength of the cured PMMA cement, the host bone, the bone insert, and the bone implant is much better in sheer and tensile strength than the host bone with only PMMA cement shown in FIG. 36.

Although the bone inserts have been illustrated with caps formed from cap micro struts, in other embodiments, the cap can be any other type of structure that provides an offset for the bone implant and fenestrations that provide liquid cement flow paths through the cap portion. With reference to FIGS. 38 and 39, an alternative embodiment of the bone insert 170 is illustrated. FIG. 38 illustrates a side view and FIG. 39 illustrates a top view of the bone insert 170. The elongated stem and barrier portions of the alternative bone insert 170 are very similar to the other illustrated bone inserts. However, the cap 171 does not include cap micro struts. In the illustrated embodiment, the cap 171 is a cylindrical structure that has a square cross section center orifice 173 that can be used as a center tool recess. In other embodiments, the cross section can be any other geometric shape. The bone insert 170 can also have a plurality of liquid cement flow paths 175 that can be in a radial pattern extending outward from the center orifice 173 to the outer cylindrical surface of the cap 171. The illustrated cap 171 can have a flat top which can be appropriate when the cap 171 diameter is smaller or alternatively, the cap 171 can have a convex spherical or aspherical upper surface. As discussed above, the upper surface of the cap 171 can provide a small focal area point of contact with the bone implant.

The elongated stem 15 of the alternative bone insert 170 can be inserted into a drilled hole in the host bone or directly into an undrilled host bone with an insertion tool having a corresponding cross section driver head. The barrier 13 can be pressed against the outer surface of the host bone to provide the desired offset of the bone implant. The bone implant can provide a small focal point of contact with the cap 171 of the bone insert. Liquid cement can be poured or injected into the center orifice 173 and can flow through the plurality of liquid cement flow paths 175 to completely fill all fenestrations in the cap 171. The bone implant can then be placed against the cap 171. The cement can cure to bond the bone implant to the bone insert 170 and the host bone. The bone insert 170 can initially be held to the host bone mechanically with the friction between the elongated stem 15 and over time host bone can grow into the surface and fenestrations in the elongated stem 15 as well as the lower ingrowth surface of the barrier 13.

With reference to FIG. 40, a side view of a bone insert 191 having a cap 11 having a hemispherical upper surface made from a plurality of cap micro struts 21. Liquid cement can surround and flow through fenestrations 23 between the cap micro struts 21. The cap micro struts 21 at bottom of the cap 11 are coupled to an upper surface of the barrier 13 which as discussed above prevents liquid cement from flowing into the stem 15 portion of the bone insert 191. The stem 15 is made from a plurality of stem micro struts 25 with stem fenestrations 27 between the adjacent stem micro struts 25. The stem micro struts 25 can have surfaces that promote bone in growth and over time, the bone can grow into the stem fenestrations 27.

Figure 41:
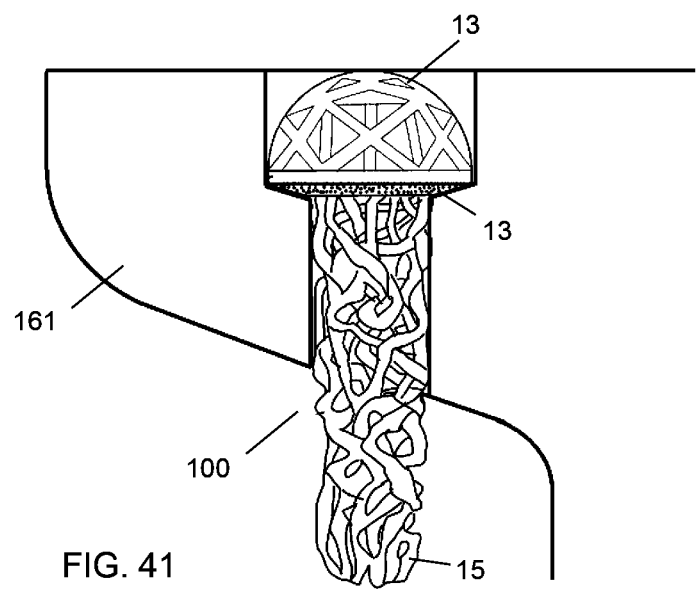
FIG. 41 illustrates a view of a bone insert in a vertical hole in bone.

The hemispherical surface of the cap 11 can be useful to provide a small point or area of contact between a bone implant and the cap 11 of the bone insert 191 which can be positioned at any angle in the bone 161. In some embodiments, the depth and angle of the bone insert can be determined to avoid surgical errors. With reference to FIG. 41, the bone insert 100 angle, depth and position are problematic because there is insufficient bone 191 thickness at the desired bone insert 100 location. If the bone insert 100 is inserted into the bone 191 at this location at a vertical angle, the stem 15 of the bone insert 100 will extend through the bone 191 which is unacceptable.

Figure 42:
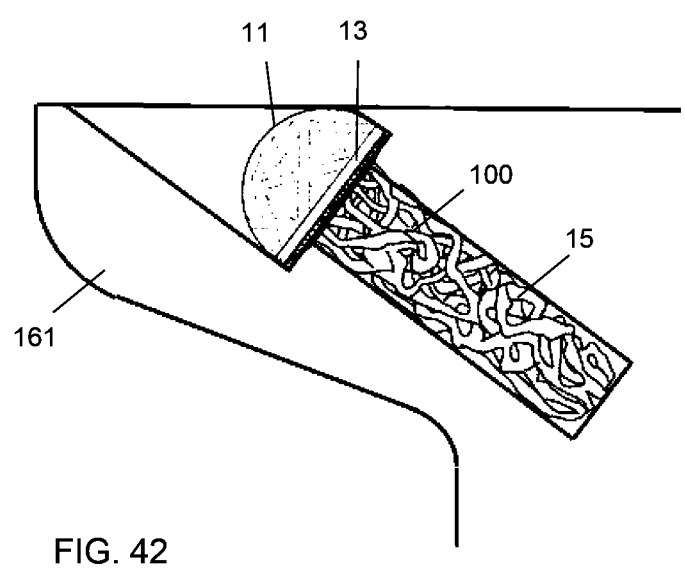
FIG. 42 illustrates a view of a bone insert in a diagonal hole in bone.

With reference to FIG. 42, in order to correct this problem, the bone 191 can be drilled at an angle and the bone insert 100 can be inserted at an angle so that the implanted bone insert 100 is positioned properly within the bone 191. The stem 15 of the bone implant 100 can have a friction fit with the inner diameter of the drilled hole and the barrier 13 can be pressed against the step formed by the drill. A small contact area on the cap 11 of the bone insert 100 can be coplanar with the resection surface of the bone 191. A planar surface of the bone implant (not shown) can then be placed onto and bonded to the resection surface of the bone 191 and the small contact area on the cap 11 of the bone insert 100 with PMMA cement. The PMMA cement can fill the hole above the step surface. However, the barrier 13 of the bone insert 100 can prevent the liquid PMMA cement from flowing into the stem 15 portion of the bone implant 100. The PMMA cement can surround all of the stem micro struts to form an interdigitated composite structure with the cap. The cured PMMA cement can bond the bone implant to the bone insert and the resection surface of the bone 191. Over time, the bone will grow into the bone ingrowth surfaces on the lower surface of the barrier 13, the stem micro struts and into the fenestrations between the stem micro struts of the stem 15. Thus, the bone implant can be secured to a much stronger structure than just PMMA cement alone.

In another embodiment, in a revision setting, after an implant has failed either cemented or non-cemented, frequently, a shell or rim of bone remains once the inflammatory tissues and or cement surrounding the bone implant have been removed. In that setting, not enough bone remains to resect bone in specific planes necessary for revision surgery. In this setting, the remaining rim may have complex and usually concave conformational geometry. After drilling into the sclerotic bone and the stem of the bone insert is inserted into the drilled hole, the bone implant is placed on the cap of the bone insert protruding into the cavity which has been left after debridement of tissues and prior removal of the original failed implant. Cement is then placed into the irregular defect and into the cap of the bone insert to stabilize the cement filling the large defect. For total knee surgery, this situation arises in locations such as the femoral condyles or specifically the posterior femoral condyles of in the tibial plateau.

Figure 34:
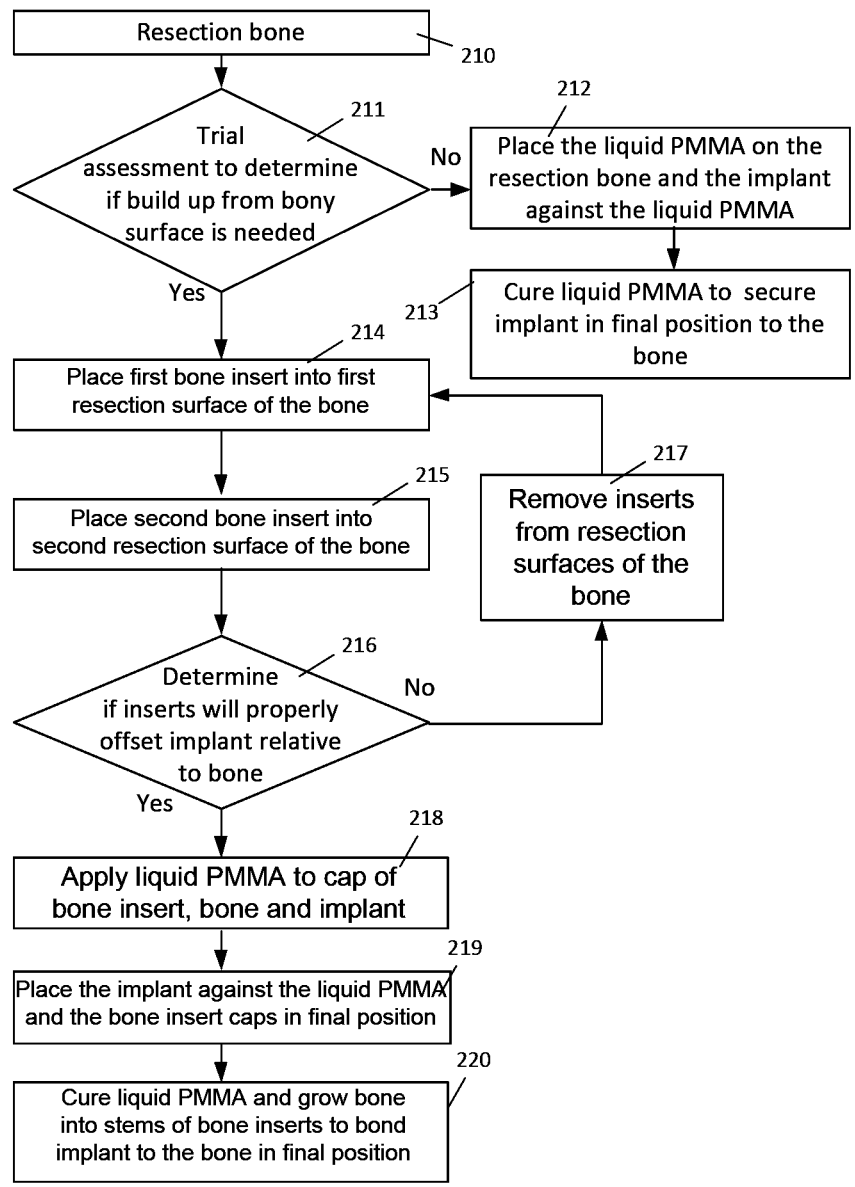
FIG. 34 illustrates a flowchart of process steps for coupling an implant to a bone with bone inserts on multiple resection surfaces.

FIG. 34 is a flowchart of process steps for coupling an implant to a bone with bone inserts on multiple resection surfaces. In this embodiment, the bone is resectioned forming multiple resection surfaces 210. Trialing is then performed to determine if the implant will be properly positioned relative to the bone or if build up from the bony resection surfaces is needed 211. If the resection bone surfaces are properly positioned and no build up from the bony surface is needed, liquid PMMA can be placed on the resection bone and the implant can be placed on the liquid PMMA and the bone 212. The liquid PMMA can then cure to secure the implant in the final position on the bone 213. In build up or an offset is needed to the resection surfaces, a first bone insert is placed in a first resection surface of the bone 214 and a second bone insert is placed in a second resection surface of the bone 215. The surgeon can then determine if the first and second inserts will properly position the implant offset relative to the bone 216. If the offset is incorrect, the inserts that need to be replaced are removed from the bone 217 and replacement first and/or second inserts are placed into the bone. If the inserts provide the proper implant offset relative to the bone, liquid PMMA cement can be applied to the PMMA portions of the inserts, bone and implant 218. The implant is placed against the liquid PMMA which can fill all gaps between the resection surface of the bone and the implant 219. The liquid PMMA cures and hardens to bond to the cured PMMA portions of the bone inserts on the first and second resection surfaces. This creates a high strength PMMA structure and secures the implant to the bone 220.

The present disclosure, in various embodiments, includes components, and apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. A bone insert comprising:
a cap having a plurality of fenestrations providing multiple flow paths through the cap for liquid cement wherein the cap contains the liquid cement in the fenestrations and surrounding a plurality of cap micro struts;
an elongated stem having bone ingrowth surface fenestrations on an outer surface of the elongated stem; and
a solid barrier structure between a lower surface of the cap and an upper surface of the elongated stem wherein the barrier physically separates the cap from the elongated stem and prevents the liquid cement from flowing from the cap into the elongated stem.

2. The bone insert of claim 1 wherein the cap has a plurality of cap micro struts that are coupled to each other at junctions to form a lattice structure.

3. The bone insert of claim 1 wherein the cap has a plurality of cap micro struts or a plurality of stem micro struts that have a cross section diameter between 25-750 microns.

4. The bone insert of claim 1 wherein an upper surface of the cap forms a convex surface that provides a focal offset for a bone implant.

5. The bone insert of claim 1 wherein the barrier structure has an outer diameter that is equal to or greater than a width of the elongated stem and equal to or greater than a width of the cap.

6. The bone insert of claim 1 wherein the liquid cement is poly(methyl methacrylate) cement.

7. The bone insert of claim 1 wherein a modulus of elasticity of the elongated stem is between 10,000 and 23,000 MPa.

8. The bone insert of claim 1 wherein a longitudinal modulus of elasticity of the elongated stem is different than a transverse modulus of elasticity of the elongated stem.

9. The bone insert of claim 1 wherein a lower surface of the barrier structure adjacent to the elongated stem has bone ingrowth surface features.

10. The bone insert of claim 1 wherein a cap micro strut volume is less than 30% of a total cap volume.

11. The bone insert of claim 1 wherein a stem micro strut volume is less than 40% of a total stem volume.

12. The bone insert of claim 1 wherein a diameter of the cap is between 5 mm and 60 mm and a diameter of the elongated stem is between 2 mm and 30 mm.

13. The bone insert of claim 1 wherein the cap includes a center orifice at a geometric center of the cap that is an inlet for the multiple flow paths through the cap for the liquid cement.

14. The bone insert of claim 1 wherein the cap has a center tool recess having a symmetric polygon cross section, wherein the symmetric polygon cross section has a geometric center that is aligned with a center axis of the cap and the elongated stem.

15. The bone insert of claim 1 wherein the cap has a plurality of cap micro struts and some of the plurality of cap micro struts form a center tool recess having a symmetric polygon cross section and an extraction surface feature, wherein the symmetric polygon cross section has a geometric center that is aligned with a center axis of the cap and the elongated stem.

16. A bone insert comprising:
   a cap having a plurality of cap micro struts and fenestrations between the plurality of cap micro struts that provide multiple flow paths through the cap for liquid cement wherein the cap contains the liquid cement in the fenestrations and surrounding a plurality of cap micro struts;
   an elongated stem having a plurality of stem micro struts and bone ingrowth surface features on outer surfaces of the plurality of stem micro struts; and
   a solid barrier structure between a lower surface of the cap and an upper surface of the elongated stem wherein the barrier physically separates the cap from the elongated stem and prevents the liquid cement from flowing from the cap into the elongated stem.

17. The bone insert of claim 16 wherein the plurality of cap micro struts have a cross section diameter between 25-750 microns and the plurality of stem micro struts have a cross section diameter between 25-750 microns.

18. The bone insert of claim 16 wherein an upper surface of the cap forms a convex surface that provides a focal offset for a bone implant.

19. The bone insert of claim 16 wherein a modulus of elasticity of the elongated stem is between 10,000 and 23,000 MPa.

20. The bone insert of claim 16 wherein a cap micro strut volume is less than 30% of a total cap volume and a stem micro strut volume is less than 40% of a total stem volume.

* * * * *